US009919910B2

(12) United States Patent
Gibson et al.

(10) Patent No.: US 9,919,910 B2
(45) Date of Patent: Mar. 20, 2018

(54) FLUID PRESSURIZATION AND DISPENSING SYSTEM

(71) Applicants: John Delano Gibson, Federal Way, WA (US); Todd Kristian Hansen, Bianbridge Island, WA (US)

(72) Inventors: John Delano Gibson, Federal Way, WA (US); Todd Kristian Hansen, Bianbridge Island, WA (US)

( * ) Notice: Subject to any disclaimer, the term of this patent is extended or adjusted under 35 U.S.C. 154(b) by 53 days.

(21) Appl. No.: 15/051,214

(22) Filed: Feb. 23, 2016

(65) Prior Publication Data

US 2017/0240405 A1    Aug. 24, 2017

(51) Int. Cl.
| | |
|---|---|
| *B67D 1/04* | (2006.01) |
| *B67D 1/00* | (2006.01) |
| *B67D 1/12* | (2006.01) |
| *B67D 1/08* | (2006.01) |
| *B67D 1/14* | (2006.01) |
| *G01N 7/00* | (2006.01) |

(52) U.S. Cl.
CPC ......... *B67D 1/0406* (2013.01); *B67D 1/0004* (2013.01); *B67D 1/0877* (2013.01); *B67D 1/125* (2013.01); *B67D 1/1477* (2013.01); *G01N 7/00* (2013.01)

(58) Field of Classification Search
CPC ... B67D 1/0406; B67D 1/1477; B67D 1/0004
See application file for complete search history.

(56) References Cited

U.S. PATENT DOCUMENTS

| | | | |
|---|---|---|---|
| 8,251,257 | B2 | 8/2012 | Oberhofer |
| 8,875,956 | B2 | 11/2014 | Haskayne |
| 9,016,528 | B2 | 4/2015 | Peirsman |
| 9,156,670 | B2 | 10/2015 | Hill |
| 9,227,827 | B1 | 1/2016 | Scott |
| 2014/0262899 | A1 | 9/2014 | Mociak |

(Continued)

OTHER PUBLICATIONS

Technical Committee of the Brewers Association, Articles: Couplers; Beer Line; Faucets, Title of the Item: "Draught Beer Quality Manual", Date: Feb. 22, 2016 last looked at on www.draughtquality.org, pp. 3 of 82, US.

(Continued)

*Primary Examiner* — Donnell Long
(74) *Attorney, Agent, or Firm* — Patentpending, PLLC; Elizabeth Reilly

(57) ABSTRACT

A fluid pressurization and dispensing system, including a coupler releasably attached to a vessel via an attachment means for securing a vacuum seal between the coupler and the vessel for maintaining pressure within the vessel, refreshing the gas composition within the vessel, and dispensing of a fluid contents externally from within the vessel without disturbing the vacuum seal. The coupler has a rigid single body unit having a tap head, a shank, and a cap which are contiguous thereof the coupler including a plurality of channels each integrally machined within an interior portion of the coupler. The system regulates a flow of gas from a pressurized gas cartridge via a gas pressure regulator, enables venting excess gas via a gas pressure relief valve, enables measurement of gas pressure within the vessel via a gas pressure gauge. Another embodiment of the system includes a coupler including a bi-level tap head.

57 Claims, 19 Drawing Sheets

(56) References Cited

U.S. PATENT DOCUMENTS

2015/0274501 A1* 10/2015 Lehman ............... B67D 1/1405
    222/556
2016/0251211 A1* 9/2016 Hill ..................... B67D 1/1252
    141/4
2017/0174495 A1* 6/2017 McIntyre ............. B67D 1/0412

OTHER PUBLICATIONS

SKS Bottle & Packaging, Inc., Articles: Cap and Neck Finishes, "SKS Bottle & Packaging, Inc." Catalog, Date: Feb. 22, 2016 last looked at on www.sks-bottle.com/aboutus.,pp. 2, Publisher SKS Bottle & Packaging, Inc., 2600 7th Avenue, Building 60 West, Watervilet, NY 12189.

Minivalve, Inc., Title: Duckbill Valves, How They Work; Umbrella Valves, How They Work; Duckbill/Umbrella Combination Valve, How They Work, Date: Feb. 22, 2016 last looked at on www.minivalve.com, pp. 5, Publisher: Minivalve, Inc. 6100 Oak Tree Boulevard, Suite 200, Cleveland, OH 44131.

* cited by examiner

# FLUID PRESSURIZATION AND DISPENSING SYSTEM

TECHNICAL FIELD

An embodiment of the present invention relates to systems for pressurizing, and dispensing a fluid contained within a vessel under pressure, for enabling maintaining a vacuum seal between a coupler and the vessel, for pressurizing a fluid contained within the vessel with a variety of gas composition sources, for pre-pressurizing and re-pressurizing the fluid contents within the vessel without breaking the vacuum seal for enabling preservation of the freshness of the fluid, maintaining a pressure within the interior of the vessel, and enabling for dispensing of the fluid from within the interior of the vessel.

BACKGROUND

It is well understood that restaurateurs, bar tenders, and micro-breweries, wine venders, home brewers, and many consumers, store and preserve various types of fluids inside of a vessel under pressure, the vessel adapted for enabling releasable attachment to a coupler. Couplers can operate with pre-pressurized gas cartridges that are utilized to tap vessels containing a fluid. The fluid can be a liquid or a gas. The liquid can be a liquid beverage, a carbonated liquid beverage, or a non-carbonated liquid beverage. An example of a carbonated liquid beverage is beer that is dispensed externally from within the vessel by means of the gas pressure and a faucet.

When the fluid is a carbonated liquid it is well known that carbonated liquids lose carbonation when exposed to oxygen and other gases in the atmosphere. In systems including a liquid which is a carbonated beverage, once the carbonated beverage is opened by the user it begins to lose the necessary carbonation causing the flavor of the carbonated beverage to change, the fizziness to lessen, the head to deplete, such that the taste to the consumer may be described as flat or bitter, watered down, even when a standard cap is maintained or reinstalled on the liquid beverage vessel.

Nitrogenated beers are usually gassed with about 70% nitrogen ($N_2$) and about 30% $CO_2$, or 75% nitrogen ($N_2$) and about 35% $CO_2$ unlike fully carbonated beers which contain 100% $CO_2$. The $N_2$ is always put into the beer by the brewer before bottling or kegging. It is not a natural part of the fermentation process.

In systems including a liquid which is beer contained in the vessel, the beer will go flat over an extended time period and will go flat as a result of oxygenation of the $CO_2$, or a $CO_2/N_2$ blend gas composition for nitro-beer, such that the resulting oxygen fills the head space above the beer in the vessel. In addition, the beer becomes more acidic which lowers the pH of the beer, because in carbonated beers the dissolved carbon dioxide forms carbonic acid in solution, which has a bitter taste. When dealing with a liquid beverage including wine, the problem is finding a gas composition including $N_2$ gas composition to discharge into the vessel to re-pressurize and freshen the wine.

The problem is finding a means to purge the head space with a volume of a gas composition to displace the oxygen with $CO_2$ when the cap is installed to maintain pressurization within the vessel containing the beer, and, accordingly, the freshness of the beer. The original seal on the vacuum cannot be reestablished once the seal is broken.

Pressurized containers for beverages are capable of maintaining internal pressure from compressed gas, for example from carbonation, or from nitrogenation, or a blend of carbon and nitrogen, and, still further from argon. However, the pressurized containers, for example, a vessel, include a limiting connecting means that is specific to a particular coupler. Closure mechanisms range from caps, twist off or pressed, to tabs which are integrally transportable or easily cleaned due to their large size and valve/dispensing system. Medium sized containers including a capacity of 32 ounces or 64 ounces of a beverage, for example, beer containers commonly known as growlers, are generally not capable of maintaining carbonation or pressurization over an extended time period and, consequentially, if the entire volume of beer is not consumed at one sitting the remainder of the beer will go flat and taste bitter due to the carbonic acid formation upon oxidation of the beer.

It is evident, there is a need for a system that implements a purge of $CO_2$ or $CO_2/N_2$, or $N_2$, within the vessel containing a carbonated liquid beverage to maintain the $CO_2$, or $CO_2/N_2$, or $N_2$, level of the liquid beverage by displacing the detrimental gas byproducts and thereby maintaining the carbonation of the liquid beverage to ensure the liquid beverage's freshness, flavor and a non-acidic pH utilizing a universal coupler.

It is known that when a growler containing beer is opened for the first time after it is initially filled, due to the oxidation process of the beer that occurs upon the beer's exposure to oxygen, the beer loses its freshness and typically goes flat within a few hours. Still further, upon filling the growler with beer the beer is oxygenated by the oxygen present in the interior of the growler and initiates the oxygenation process of the beer. Accordingly, when the beer is dispensed from the growler there is a loss of $CO_2$ from within the growler and the beer which enables increasing the imbalance of carbonation of the beer and depletion of the freshness of the beer.

Attempts have been made to improve the preservation of liquid beverages contained in a vacuum sealed vessel. Many of these systems include couplers comprising separate components engaged to each other to facilitate operability and include couplers compatible with a specific liquid vessel, for example, a glass growler. More particularly, these couplers are restricted to implement a particular type of gas cartridge.

However, no solution is available in the art for providing a coupler implemented in a single body unit including a tap head, shank, cap, gas inlet, carbonation port, gas pressure gauge, gas pressure relief valve, gas pressure regulator, fluid delivery tube, adaptor, and faucet that can provide a system to accommodate a variety of pre-pressurized gas composition cartridges. Particularly, the problem of efficiently discriminating the gas composition content within the vessel is still unresolved. In addition, no solution is available in the art for providing a coupler that can be releasably attached to a variety of liquid vessels having a variety of neck finishes. In this context, it would be desirable to provide a coupler that can be implemented on a variety of liquid vessels and be operable to engage a variety of pressurized gas composition cartridges housing selective gas compositions including $CO_2$, $CO_2$ and $N_2$; $N_2$, and argon, and more particularly, with preferred gas compositions of 75% $N_2$ and 25% $CO_2$ which an embodiment of this disclosure herein provides.

All of the above hinders the liquid dispensing application of currently available couplers for maintaining the freshness of a liquid beverage. Therefore, there is a long felt need for a system that vacuum seals a coupler to a vessel for preserving and maintaining freshness of the fluid contents of the vessel by enabling maintaining pressurization within the vessel and enabling dispensing of the fluid contents externally from within the vessel without breaking the vacuum seal between the coupler and the vessel.

SUMMARY

An embodiment of the present invention proposes a fluid pressurization and dispensing system for pressurizing a fluid contained in a vessel without comprising a vacuum seal between a coupler releasably attached to the vessel. The fluid pressurization and dispensing system enables maintaining pressurization within the vessel as needed, and enables dispensing of the fluid externally from within the vessel. The fluid pressurization and dispensing system, also, enables implementation of a variety of pre-pressurized gas composition cartridges. In addition, an adaptor is implemented in an embodiment of the fluid pressurization and dispensing system for enabling releasably attaching the coupler to a variety of commercially available vessels.

In general, the present embodiment of the present invention disclosure pertains to systems for pressurizing a fluid, preserving the freshness of the fluid, storing the fluid, and dispensing the fluid over a short period of time. The fluid can include any one of the following, including: a liquid, a liquid beverage for consumption, a carbonated liquid beverage, a non-carbonated liquid beverage, and a gas. In some implementations of the embodiments presented, the fluid dispensing system are configured for storing carbonated liquids, and include a container capable of maintain an internal pressure in a head space above the liquid. In embodiments of the present invention, a fluid delivery system, also, include a delivery device configured to allow a user to easily dispense a liquid from the container under pressure and/or a device configured to allow the container to be pressurized as the volume of the liquid contained in the container are exhausted.

According to one aspect of the present disclosure, the fluid pressurization and dispensing system comprises, a coupler including a rigid unitary body having an exterior surface surrounding a solid interior portion wherein a plurality of channels are integrally machined within, wherein the coupler is operably connected to a vessel through an attachment means for securing a vacuum seal between the coupler and the vessel for enabling maintaining a pressure within the vessel and for dispensing of a fluid contents externally from within the vessel.

The coupler has generally a T-shape further comprising a tap head which defines an upper horizontal cylindrical portion of the coupler, a cap which defines a lower dome portion of the coupler, a shank which defines a vertical cylindrical waist portion of the coupler is arranged being orientated vertically between the tap head and the cap, wherein the tap head, the shank and the cap are contiguous thereof the coupler.

The cap further includes a crown defining a top portion of the cap, an outer sole defining a flat annular outer margin of the cap, a skirt defining a circumferential periphery of the cap between the crown and the outer sole, an inner sole defining a flat annular inner margin of the cap, wherein the inner sole includes a plurality of ports including a at least one gas inlet port and a at least one carbonation port integrally machined within the inner sole, a bore hole circumvented by a hose barb centrally disposed within the inner sole, a plug includes a plug opening circumvented by a rigid cylindrical sidewall having an exterior side coaxial with an interior side projecting from between the outer sole and the inner sole of the cap.

The tap head includes a posterior opening integrally machined within a posterior end of the tap head and an anterior opening integrally machined within an anterior end of the tap head. A faucet operatively connected to the anterior opening of the tap head via an attachment means is adapted for enabling receiving the fluid contents from within the vessel and adapted for dispensing the fluid externally from the interior vessel.

A gas composition cartridge is operatively connected and fluidly communicative to a gas injection aperture integrally machined within the tap head. The gas injection aperture includes a fistula having an orifice, the fistula adapted and operable for puncturing a pressurized gas composition cartridge removably operatively connected thereon such that a flow of gas composition is released passing through the orifice;

A gas pressure regulator is maintained in a seat integrally machined within the tap head extending from the posterior opening of the tap head. The seat is adapted and operative for seating the gas pressure regulator via an attachment means, wherein the gas pressure regulator including a gas pressure regulator valve and a gas pressure regulator chamber is adapted and operable for regulating the flow of gas composition from the pressurized gas composition cartridge through the gas pressure chamber and into the vessel.

A gas flow channel is a first of the plurality of channels integrally machined within the interior portion of the coupler. The gas flow channel includes an upper gas flow channel, and a lower gas flow channel terminating at a gas inlet port integrally machined within the inner sole of the cap, wherein the upper gas flow channel is operatively fluidly communicable to the pressurized gas composition cartridge for enabling transmission of the flow of gas composition from the pressurized gas composition cartridge through the upper gas flow channel and into the gas pressure regulator chamber, and the lower gas flow channel operatively fluidly communicable to the gas pressure regulator chamber for enabling transmission of the flow of gas composition from the gas pressure regulator chamber through the lower gas flow channel through the gas inlet port and into the vessel.

A rotary actuator is operatively releasably attached to the gas pressure regulator via an attachment means for enabling manual regulation by a user of the flow of gas composition from the upper gas flow channel through the gas pressure regulator chamber and into the lower gas flow channel for selectively dispensing a predetermined volume of gas composition pressure into the vessel for maintaining a regulated pressure within the vessel.

A gas pressure gauge is releasably attached via an attachment means to a gas pressure aperture integrally machined within the cap.

A second channel of the plurality of channels is a gas pressure channel integrally machined within the cap extending from the gas pressure aperture to a gas pressure gauge port integrally machined within the inner sole of the cap, wherein the gas pressure channel is adapted for enabling transmission of a gas pressure from within the vessel through the gas pressure gauge port and through the gas pressure channel for measuring by the gas pressure gauge.

The gas pressure relief valve is releasably attached via an attachment means to a gas pressure relief aperture integrally machined within a the cap for enabling one-directional release of a gas composition externally from within the vessel, wherein an activation component operatively attached to the gas pressure relief valve is activated upon exceeding a predetermined gas pressure level within the vessel.

A third of the plurality of channels is a gas pressure relief valve channel integrally machined within the cap extending from the gas pressure relief valve aperture to a gas pressure relief port integrally machined within the inner sole of the cap, wherein the gas pressure relief valve channel is adapted for enabling transmission of the one-directional release of gas composition externally from within the vessel through the gas pressure relief port through the gas pressure relief valve channel and through the gas pressure relief valve.

A fourth of the plurality of channels is a fluid delivery channel integrally machined within the coupler, the fluid delivery channel having a primary opening and a terminal opening, the primary opening commensurate with the bore hole centrally disposed within the cap, and the terminal opening commensurate with the anterior opening of the tap head, the fluid delivery channel includes a fluid delivery inlet runner fluidly communicable to a fluid delivery outlet runner adapted and operable for directing transmission of the fluid contained within the vessel upstream to the faucet.

A fluid delivery tube is provided having a first end having a first opening operatively connected to the hose barb circumventing the bore hole and a second end having a second opening provided immersed within the fluid contained within the vessel for enabling delivery of the fluid contained within the vessel therethrough to the fluid delivery channel.

The vessel further comprises a unitary body capable of being pre-pressurized including double sidewalls terminating at a base having an interior cavity operable to maintain a fluid therein under pressure; a neck having upstanding side walls proud of a shoulder portion of the vessel having an opening defined by a circumferential rim, wherein the neck opening is fluidly communicable to the plurality of ports including the at least one gas inlet port integrally machined within the inner sole when the coupler is releasably attached to the vessel under the vacuum seal; and a chime permanently mounted to the shoulder portion of the vessel for enabling handler holds for transporting the fluid pressurization and delivery system.

In another embodiment of the fluid pressurization and dispensing system, the coupler comprises a bi-level tap head.

These and other aspects, features, and benefits of the claimed invention(s) will become apparent from the following detailed written description of the preferred embodiments and aspects taken in conjunction with the following drawings, although, variations and modifications thereto may be effected without departing from the spirit and scope of the novel concepts of the disclosure. A detailed description of certain exemplary embodiments of the present system is provided below in reference to the various patent figures and illustrations.

BRIEF DESCRIPTION OF THE DRAWINGS

In the accompanying drawings, which illustrate one or more example embodiments.

DETAILED DESCRIPTION

Figure 1:
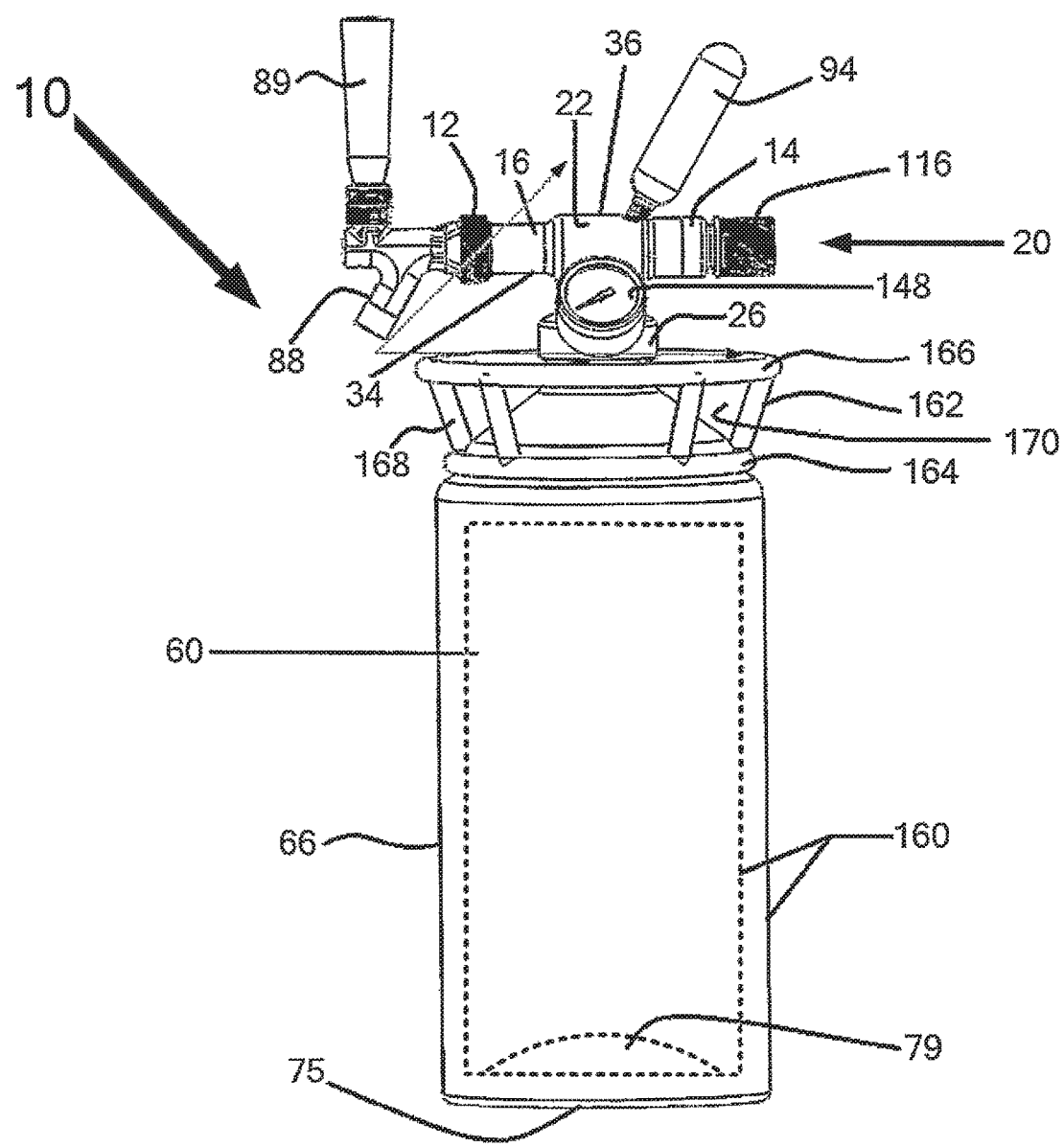
FIG. 1 illustrates an isometric view of a front perspective view of an embodiment of the fluid pressurization and dispensing system showing a coupler and a vessel in use.

It will be appreciated that, although, specific embodiments of the present disclosures are described herein for purposes of illustration, various modifications may be made without departing from the spirit and scope of the present disclosure. Accordingly, the present disclosure is not limited except as by the appended claims.

The fluid pressurization and dispensing system and components described herein are primarily intended for use with fluids, including consumable liquids and beverages, but can, also, be used to dispense any fluid, such as, liquids, gases, solvents, cleaning fluids, and any combination thereof. Thus, although this disclosure proceeds with reference mainly to liquid beverages, one of ordinary skill in the art will understand that the inventive features disclosed herein can similarly be applied to these analogous fields of endeavor.

Referring to FIGS. 1-16 a fluid pressurization and dispensing system 10 according to an embodiment of the invention will be described in the following disclosure. The fluid pressurization and dispensing system 10 including a coupler 20 releasably attached to a vessel 60 for securing a vacuum seal between the coupler 20 and the vessel 60 for enabling maintaining a pressure within the vessel 60 and enabling dispensing of a fluid 186 content externally from within the vessel 60.

The vessel 60 and the coupler 20 are manufactured of food-grade materials, preferably, stainless steel. The coupler 20 is portable and transferable for use with a plurality of conventional vessels 60 for containing fluids 186 wherein the coupler 20 can further include an attachment means for enabling releasably attaching the coupler 20 to a plurality of conventional vessels. The coupler 20 in another embodiment of the present disclosure includes an adaptor (not shown) for releasably connecting the coupler 20 to any one or more of a variety of commercially available vessels 60 capable of containing a fluid 186 under pressure, explained in more detail below.

FIGS. 1-5 and 8 respectively show perspective front, rear, side, top plan, bottom plan, and sectional views of the fluid pressurization and dispensing system 10. The fluid pressurization and dispensing system 10 includes the coupler 20 releasably threadably attached to the vessel 60 in use in a working closed position.

Referring to FIGS. 1-3 and FIG. 8 the fluid pressurization and dispensing system 10 is shown including the vessel 60 vacuum sealed to the coupler 20 in use in a working closed position such that a vacuum seal is maintained. According to one aspect the fluid pressurization and dispensing system 10 is implemented to pressurize various types of fluids 186 contained in the vessel 60 under pressure, for pre-pressurizing the vessel 60, for preserving the fluid 186 contents within the vessel 60, maintaining adequate pressurization within the vessel 60, re-pressurizing the fluid 60 contained within the vessel 60, and dispensing of the fluid 186 contents externally from within the vessel 60.

Figure 6:
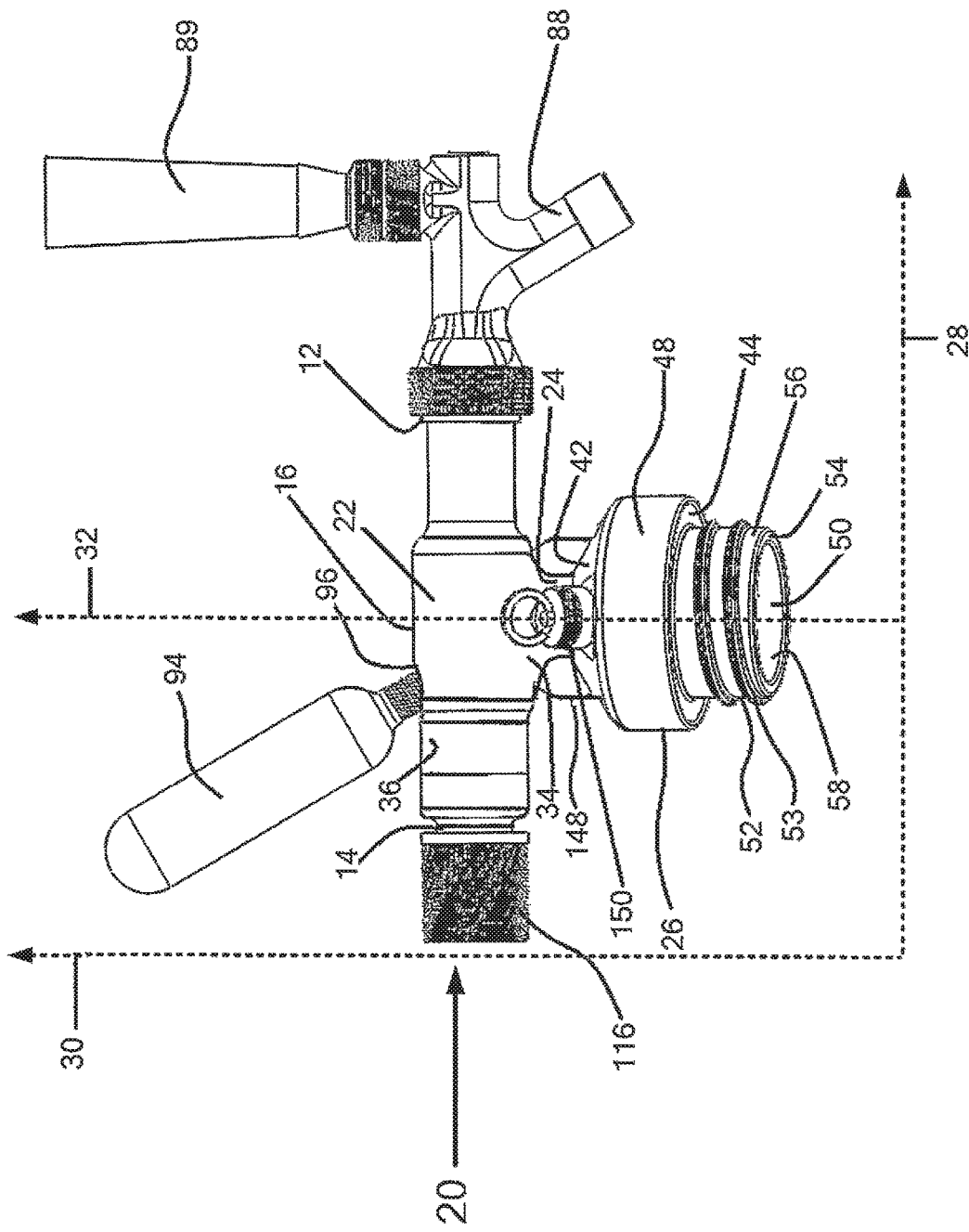
FIG. 6 illustrates a rearward side elevation of a coupler in isolation, according to one embodiment of the present disclosure.
Figure 7:
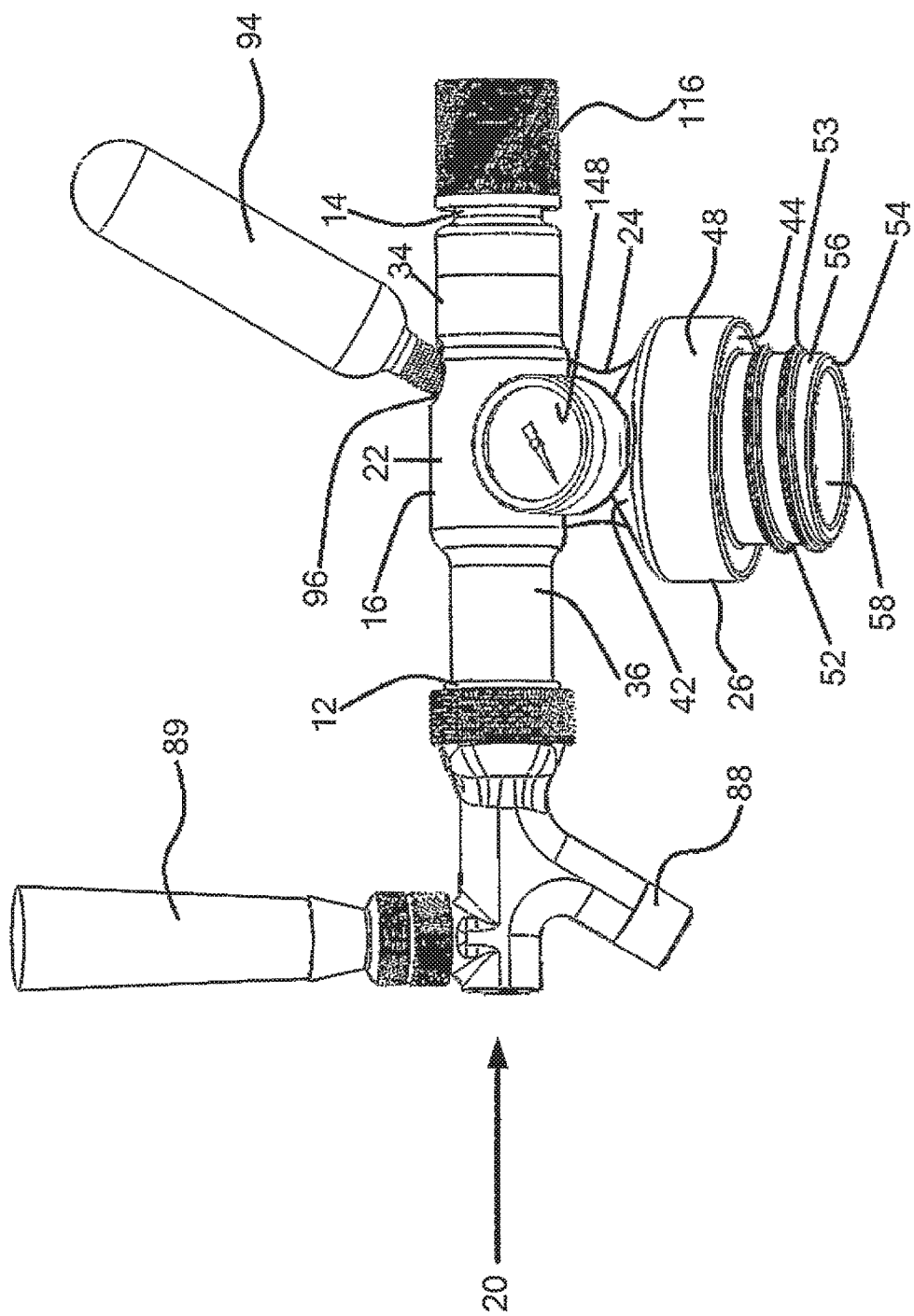
FIG. 7 illustrates a forward side elevation of the coupler in isolation, according to one embodiment of the present disclosure.
Figure 16:
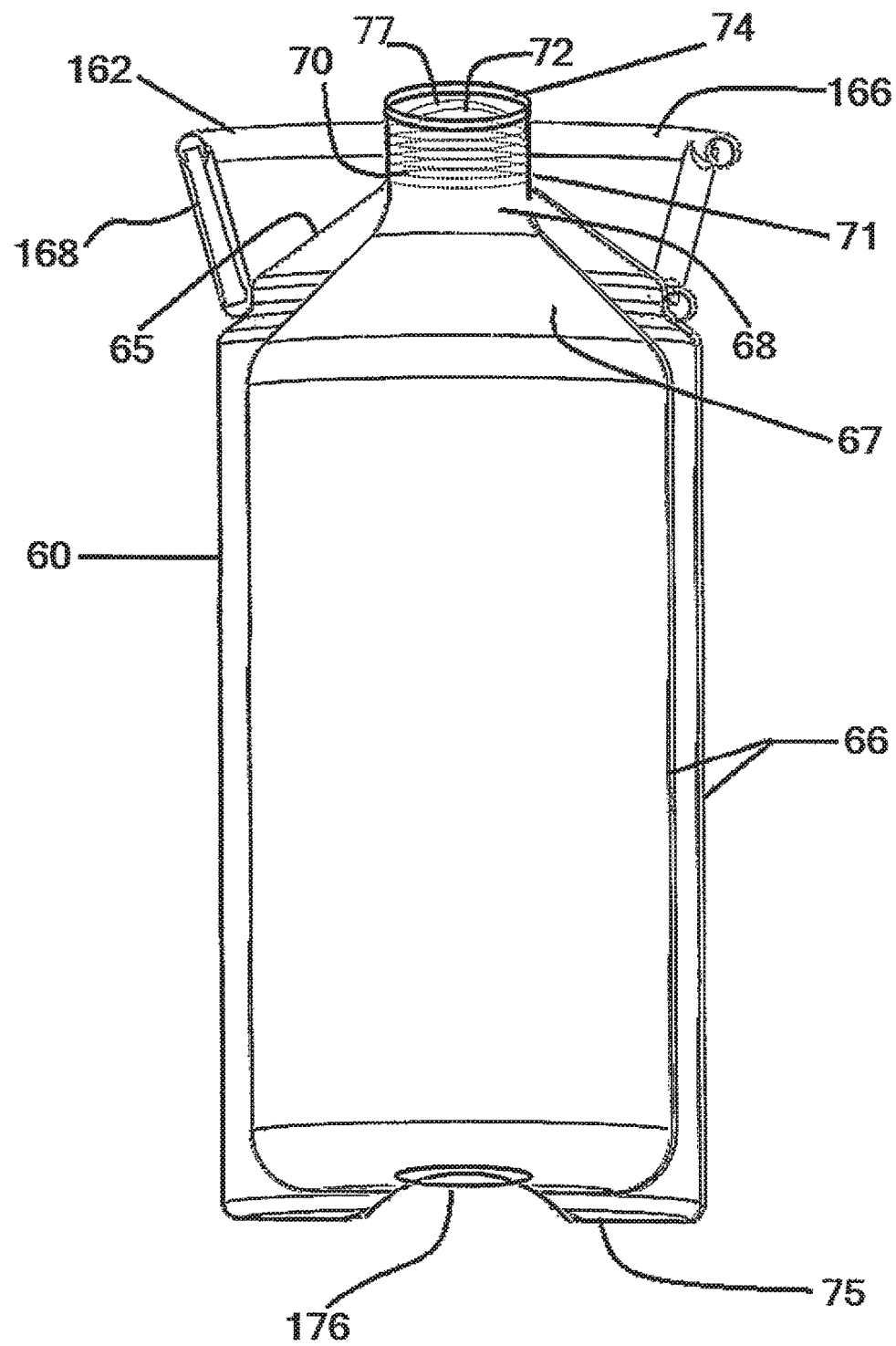
FIG. 16 is a perspective view of a vessel half in isolation, according to an embodiment of the present disclosure.

As shown in FIGS. 1-3 and FIGS. 6-8 and 16, the coupler 20 having a plug opening 50 is releasably attached to a neck opening 72 of the vessel 60 via an attachment means discussed in more detail below with FIGS. 6-7 and 16. The vessel 60 and the coupler 20 are manufactured of food-grade materials, preferably, stainless steel. The coupler 20 is portable and transferable for use with a plurality of conventional vessels 60 for containing fluids wherein the coupler 20 can further include an attachment means for enabling releasably attaching the coupler 20 to a plurality of conventional vessels 60.

FIGS. 6-8, and FIGS. 10-16 more particularly illustrate an exemplary embodiment of the coupler 20 according to an embodiment of the present disclosure. The coupler 20 includes a rigid single body unit having generally a "T" shape having a mass with a surface density, a y-axis 30, an x-axis 28, a centroidal axis 32, an exterior surface 16 which surrounds an interior portion 18 which is solid wherein a plurality of channels are each integrally machined within the coupler 20, and each having a hollow tubular configuration extending therethrough the coupler 20 from the exterior surface 16 therethrough the solid interior to another portion of the exterior surface 16. Accordingly, each of the plurality of channels is separately and rigidly autonomously supported within the coupler 20 for enabling proper function of each of the plurality of channels, discussed in more detail below.

The coupler 20 is a rigid single body unit comprising including having generally a "T" shape. The coupler 20 includes a tap head 22, a shank 24, and a cap 26 wherein the tap head 22, the shank 24, and the cap 26 are contiguous thereof the coupler 20. The coupler 20 includes the exterior surface 16 which surrounds the interior portion 18 which is solid, wherein the solid interior portion the plurality of channels are each integrally machined within the solid interior portion 18 of the coupler 20.

In the depicted embodiments, the tap head 22 defines an upper horizontal cylindrical portion of the coupler 20 having an anterior end 12 and a posterior end 14, the tap head 22 having a length $L^1$ extending therebetween and laterally along the x-axis 28, a ventral side 34 and a dorsal side 36 having a cross-diameter ($CD^1$), the anterior end 12 having an anterior opening 38 and the posterior end 14 having a posterior opening 40.

Immediately descending from the coupler 20 is the shank 24. The shank 24 defines a vertical cylindrical waist portion of the coupler 20 including a proximal end 25 and a distal end 27 having a length $L^2$ therebetween and a cross-diameter ($CD^2$), the proximal end 25 of the shank 24 extends axially towards the ventral side 34 of the tap head 22 and the distal end 27 of the shank 24 extends axially to the cap 26 along the centroidal axis 32. The shaft 24 provides a height to the coupler 20 such that when a user is dispensing a fluid from the fluid pressurization and dispensing system 10 a receptacle can easily be placed under a faucet 88 operatively connected to the coupler 20.

Immediately descending from the shaft is the cap 26, as illustrated more particularly in FIGS. 6-7, 9-11 and 13-15. The cap 26 defines a lower dome portion of the coupler 20. The cap 26 includes a crown 42 defining a top portion of the cap 26, an outer sole 44 defining a flat annular outer margin of the cap 26, a skirt 48 defining a bottom circumferential periphery of the cap 26 between the crown 42 and the outer sole 44, an inner sole 46 defining a flat annular inner margin of the cap 26, wherein the inner sole 46 includes a plurality of ports including at least one gas inlet port 112 and a carbonation port 114 integrally machined within the inner sole 46 of the cap 26.

Figure 8:
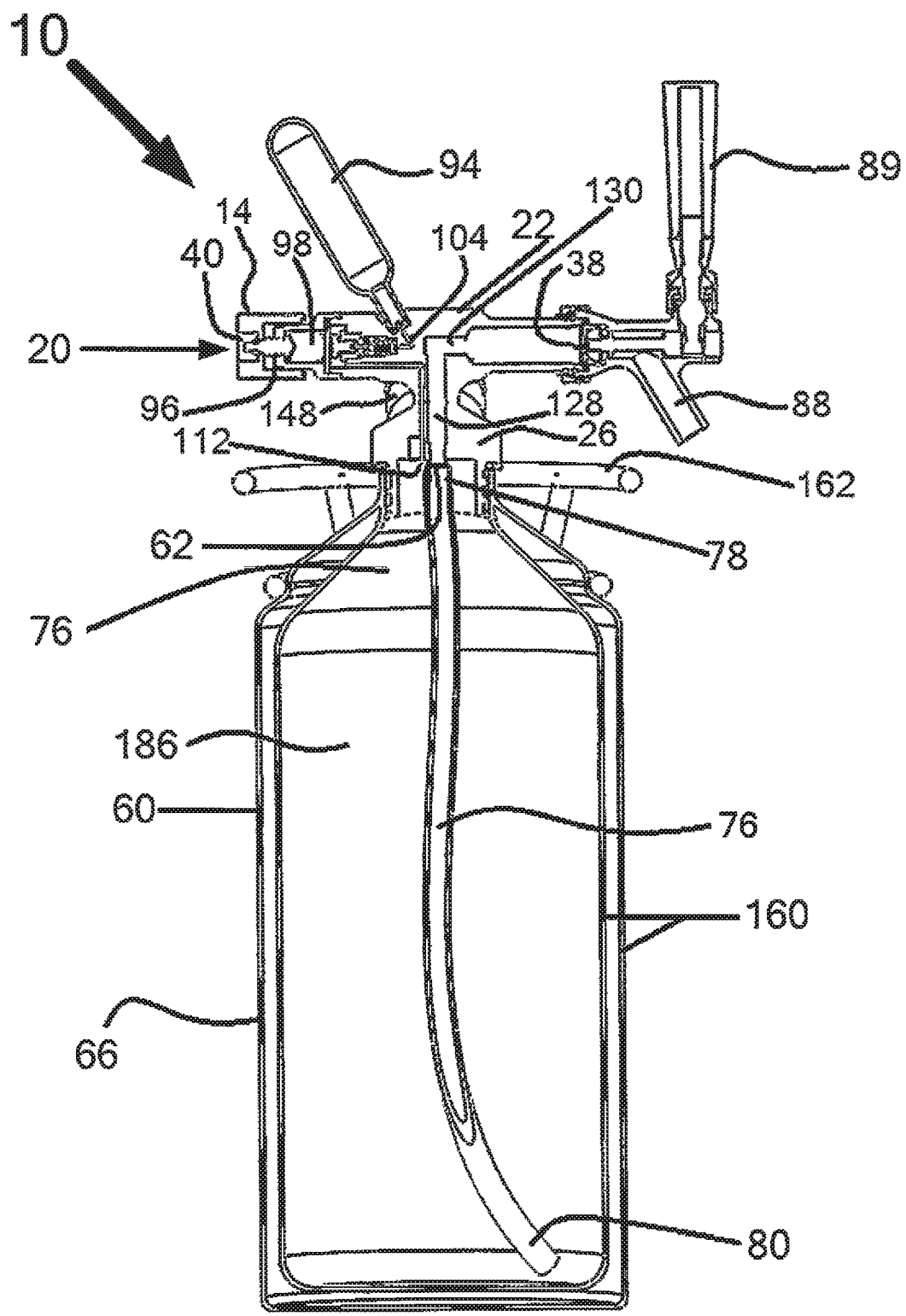
FIG. 8 is a sectional view of the fluid pressurization and dispensing system half of FIG. 2, according to one embodiment of the present disclosure.
Figure 9:
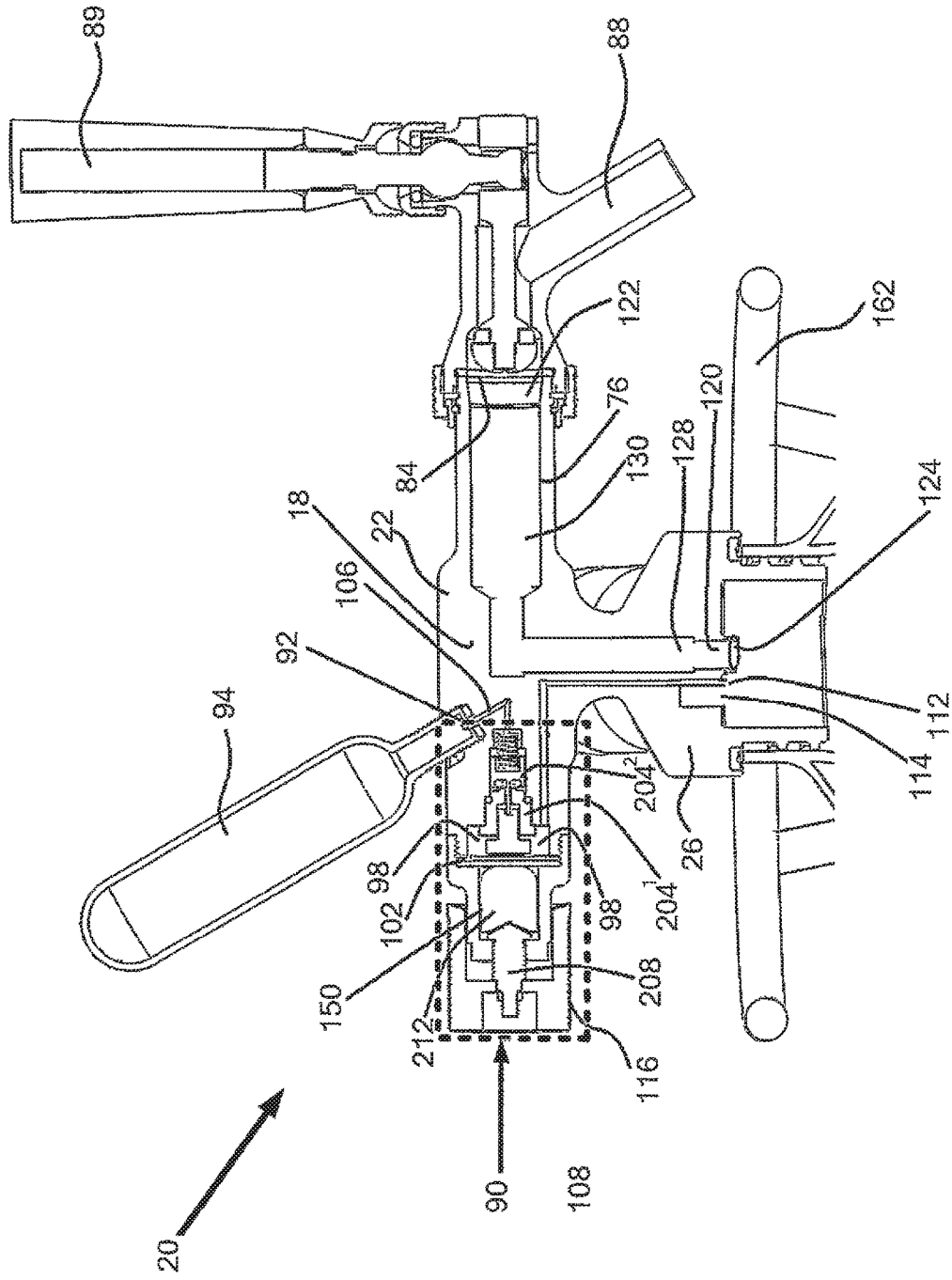
FIG. 9 is a sectional view of the coupler half of FIG. 6, according to one embodiment of the present disclosure.

The cap 26, also, includes a bore hole 62 circumvented by a hose barb 82 centrally disposed within the inner sole 46. In addition, a plug 52 includes a plug opening 50 circumvented by a rigid cylindrical sidewall having a plug finish 53 having an exterior side 56 coaxial with an interior side 58 projecting a length $L^3$ from between the outer sole 44 and the inner sole 46 of the cap 26 and having a cross-diameter ($CD^3$);

The bore hole 62 is integrally machined within a central portion within the inner sole 46 of the cap 26 along the centroidal axis 32. A fluid delivery tube 76 is releasably attached to the hose barb 36 circumventing the bore hole 62, as shown in FIG. 8.

As illustrated in FIGS. 6-8 and 16, in an exemplary embodiment of the present disclosure, the plug 52 has a plug finish 53 including an exterior threaded plug finish 55 that are compatible with a neck finish 73 of the vessel 60 having an interior threaded finish 73 of the neck 68 that function as the leak proof sealing point for the coupler 20 therewith the vessel 60 and operable to establish and maintain the vacuum seal of the vessel 60 while under pressure. In this exemplary embodiment, the plug 52 includes the plug opening 50 having a cross-diameter ($CD^3$) less than the cross-diameter ($CD^5$) of a neck opening 72 of the vessel 60 adapted to be insertable within the neck opening 72 of the vessel 60 for enabling securing a vacuum seal.

In another embodiment of the present disclosure, the coupler 20 includes the plug 52 having a plug opening 50 having a cross-diameter ($CD^3$) greater than the cross-diameter ($CD^5$) of the neck opening 72 adapted to fit over the neck opening 72 of the neck 68 of the vessel 60 for releasably attaching the coupler 20 to the vessel 60 for enabling securing a vacuum seal.

In the depicted embodiment of the present disclosure in FIGS. 6-8 and 13, the plug 52 includes a plug finish 53 having exterior threads 55 disposed on the exterior side 56 of the plug 52 having a plug opening 50 having a cross-diameter ($CD^3$) which is slightly less than the cross-diameter ($CD^5$) of the neck opening 72. The exterior threads 55 of the plug finish 53 are compatible with interior threads 77 of the neck finish 73 disposed on an interior of the neck opening 72 of the vessel 60 such that when the plug 52 is threadably attached within the neck opening 72 of the vessel 60 the vacuum seal is secured and maintained between the coupler 20 and the vessel 60.

In the exemplary embodiment of the present disclosure, the plug 52 includes a cylindrical side wall 54 which is configured and operable to provide an attachment means having a cylindrical sidewall 54 circumventing an opening 50 that is adapted for inserting into the neck opening 72 of the vessel 60. The cap 26 including the outer sole 44 defining the outer annular margin of the cap 26 receives the circumferential rim 74 of the vessel 60 and is configured to seal against the circumferential rim 74 of the vessel 60 to maintain the vacuum seal between the coupler 20 and the vessel 60.

In an embodiment of the present invention, the plug finish 53 includes threads having a 2 thread turns with buttress finish and thick threads for enabling the coupler 20 for releasably attaching to a variety of vessel types. In another embodiments of the present disclosure, additional neck finishes 70 and plug 52 finishes are described in more detail below.

Referring to FIGS. 9-11 and FIGS. 14-15, in the exemplary embodiment of the present disclosure, the fluid pressurization and dispensing system 10 includes a carbonation port 114 which is integrally machined within the inner sole 46 of the cap 26. A carbonation tube (not shown) can be releasably attached to the carbonation port 114 for enabling transmission of a selected gas composition from a pressurized gas source to be dissolved into the fluid 186 contained in the vessel 60. The carbonation port 114 includes an opening fluidly communicable with the interior of the vessel 60. A carbonator tube (not shown) is releasably attached to the carbonation port 114 disposed within the cap 26 on one end and a second end of the carbonator tube immersed within a volume of a fluid 186 is immersed within the fluid 186 contained within the vessel 60 to be treated for carbonation.

In an embodiment of the present disclosure, the fluid 186 contained in the vessel can be a carbonated liquid beverage, for example, beer. As the beer remains in the vessel 60, the beer can be exposed to an oxygen source which can be detrimental due to oxygenation of the beer causing the beer to become flat and bitter. In addition, as the carbonated beer remains in the vessel 60 for a period of time, the CO2 can break down and form carbonic acid and accordingly the pH of the beverage changes and, as a consequence, the beer can taste bitter to the consumer.

To solve this problem, the coupler 20 releasably attached to the vessel 60 in the working closed position is adapted and operable to allow the user to transmit a gas composition into the head space 67 of the vessel 60 without opening the fluid pressurization and dispensing system 10 for enabling pressurization of the vessel 60 and thereby providing a purge of gas composition, for example, $CO_2$, to the beer contained within the vessel 62. Accordingly, the carbonation of the beer is refreshed and the beer can maintain its pH and its flavor over the period of time it is contained within the vessel 60.

To implement the pressurization within the vessel, the coupler 20 includes a gas pressure aperture 140. Pressurization can be achieved by means of the pressurized gas composition cartridge 94 releasably attached to the gas injection aperture 98 integrally machined within the tap head 22 of the coupler 20.

In the depicted embodiment, referring to FIGS. 1-2, 4, 6-11 and 13 the coupler 20 includes the gas injection aperture 96 disposed within a dorsal side 36 of the tap head 22. The gas injection aperture 96 is compatible with a disposable pre-pressurized gas composition cartridge 94 that allows the user to easily dispense a regulated volume of a flow of gas composition into the vessel 60 without disturbing the vaccum seal between the coupler 30 and the vessel 60. The gas composition source of the pressurized gas composition cartridges 94 will be discussed in more detail below.

In the preferred embodiment of the present disclosure, the gas injection aperture 96 includes threads integrally machined within the dorsal side 36 of the tap head 22, wherein the gas injection aperture 96 includes a fistula 92 having an orifice, the fistula 92 configured with a sharp end adapted and operable for puncturing the pressurized gas composition cartridge 94 releasably threadably attached thereon such that a flow of gas composition is released passing through the orifice.

The gas injection aperture 96 includes the fistula 92 configured with the sharp end positioned to receive the closed pressurized gas composition cartridge 94 containing a gas composition such that when the pressurized gas composition cartridge 94 is mounted upon the fistula 92 the closed portion of the pressurized gas composition cartridge 94 is punctured and a flow of gas under pressure is released through the orifice into a gas pressure regulator 90 by means of passage through a gas flow channel 104.

More particularly, the gas flow from the pressurized gas composition cartridge enters an upper gas flow channel 106. The gas injection aperture 96 is fluidly communicable with the upper gas flow channel 106 for enabling the transmission of the gas flow composition to pass from the pressurized gas composition cartridge 94 into the upper gas flow channel 106.

In an exemplary embodiment of the present disclosure, the gas injection aperture 96 includes a threaded female attachment means integrally machined into the tap head 22 including a fistula 92 adapted to and operable to releasably attach a threaded male attachment means of a pressurized gas composition cartridge 94. In another embodiment, the gas injection aperture 96 includes a threaded male attachment means including a fistula 92 adapted to and operable to releasably attach a threaded female attachment means of a pressurized gas cartridge 94.

Figure 10:
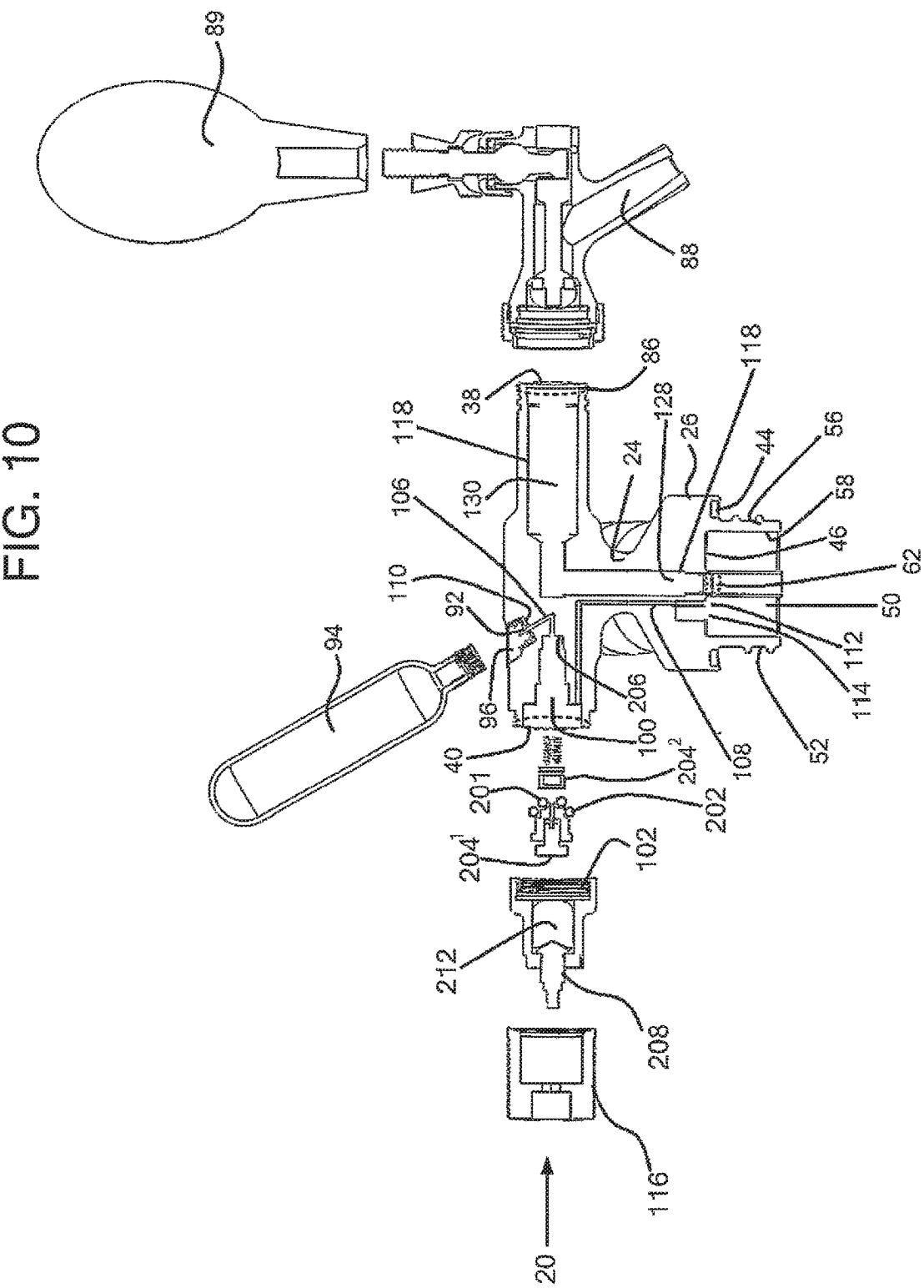
FIG. 10 is an exploded view of the coupler half of FIG. 9, according to an embodiment of the present disclosure.
Figure 11:
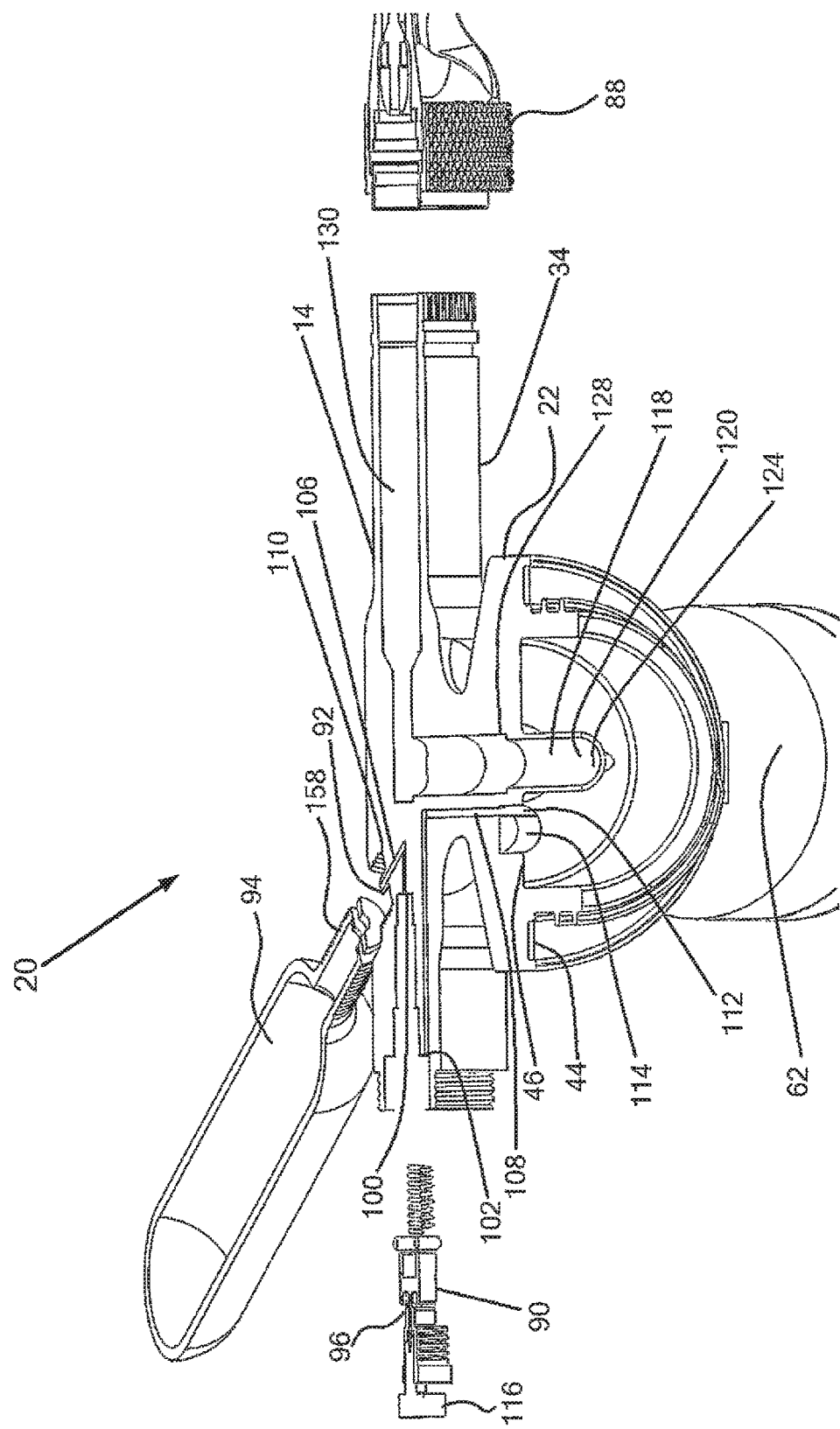
FIG. 11 is a perspective view of a coupler half illustrating integrally machined seat, gas flow channel, inlet gas port, carbonation port, bore hole, fluid delivery tube, of the coupler, according to one embodiment of the present disclosure.
Figure 12:
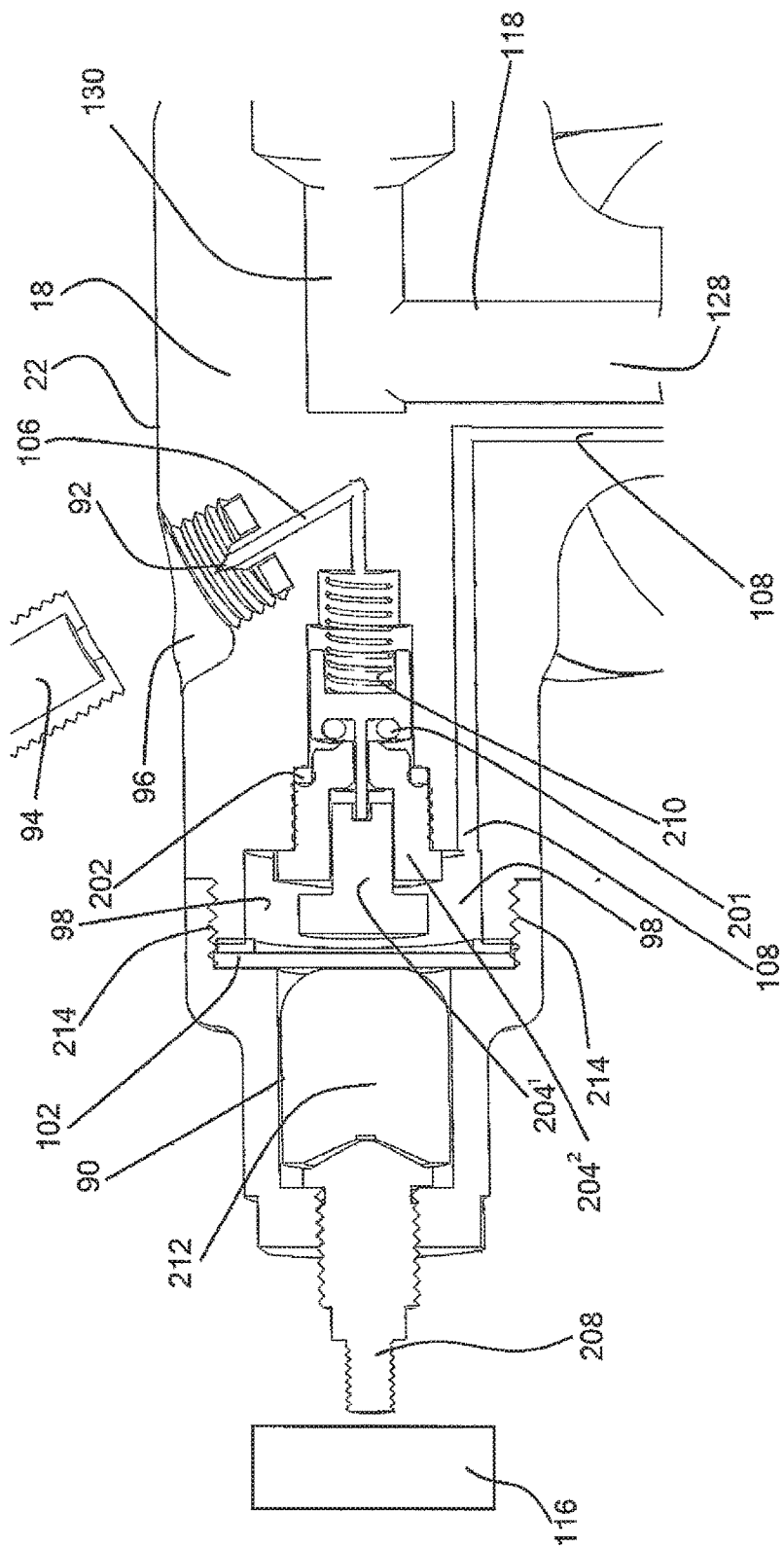
FIG. 12 is a perspective view of a gas pressure regulator half within the tap head half, according to one embodiment of the present disclosure.

As shown more particularly in FIGS. 10-12, a seat 100 is integrally machined within the tap head 22 extending from the posterior opening 40 adapted and operative for releasably attaching a gas pressure regulator 90 via an attachment means. The gas pressure regulator 90 includes a gas pressure regulator valve 211 and a gas pressure regulator chamber 98 and operable for regulating the flow of gas composition.

A first channel of the plurality of channels is the gas flow channel 104 integrally machined within the interior portion 18 of the coupler 20. The gas flow channel 104 includes an upper gas flow channel 106 having a first bend, and a lower gas flow channel 108 having a second bend, wherein the upper gas flow channel 106 is operatively fluidly communicable to the orifice of the gas injection aperture 96 for enabling transmission of the flow of gas composition from the pressurized gas composition cartridge 94 through the upper gas flow channel 106 and into the gas pressure regulator chamber 98. The lower gas flow channel 106 is operatively fluidly communicable to the gas pressure regulator chamber 98 for enabling transmission of the flow of gas composition from the gas pressure regulator chamber 98 through the lower gas flow channel 106 through the gas inlet port 112 and into the vessel 60.

The gas pressure regulator 90 includes a rotary actuator 116 operatively releasably attached to the gas pressure regulator 90 via an attachment means for enabling regulation of the flow of gas composition from the upper gas flow channel 106 through the gas pressure regulator chamber 98 and into the lower gas flow channel 106 for selectively dispensing a predetermined volume of gas composition pressure into the vessel 60 for maintaining a regulated pressure within the vessel 60.

Referring to FIGS. 1-2 and FIGS. 8-12 the rotary actuator 116 is releasably attached axially to the gas pressure regulator 90 from the posterior end 40 of the tap head 22. The rotary actuator 116 is configured to engage the gas pressure regulator 90 for enabling the user to manually regulate the transmission of the flow of gas composition from the pressurized gas composition cartridge 94 into the gas pressure regulator chamber 98 and into the interior 64 of the vessel 60 via the gas flow channel 104 and the gas inlet port 112.

More particularly, the rotary actuator 116 is adapted and operable for regulating the flow of gas composition provided by the pressurized gas composition cartridge 94 between the upper gas flow channel 106 through the gas pressure regulator chamber 98 and into the lower gas flow channel 108 through the gas inlet port 112 and into the vessel 60 by the user rotating the rotary actuator 116 a pre-calculated degree and thereby adjusting the volume of the flow of gas composition purged into the head space 76 of the vessel 60 for maintaining a regulated pressure within the vessel 60 by purging additional flow of gas composition into the vessel 60 for re-pressurizing the fluid 186 contents contained within the vessel 60.

The rotary acutator can include indicia printed thereon commensurate with a pre-set volume of gas composition to be purged into the head space 67 within the vessel 60.

Figure 13:
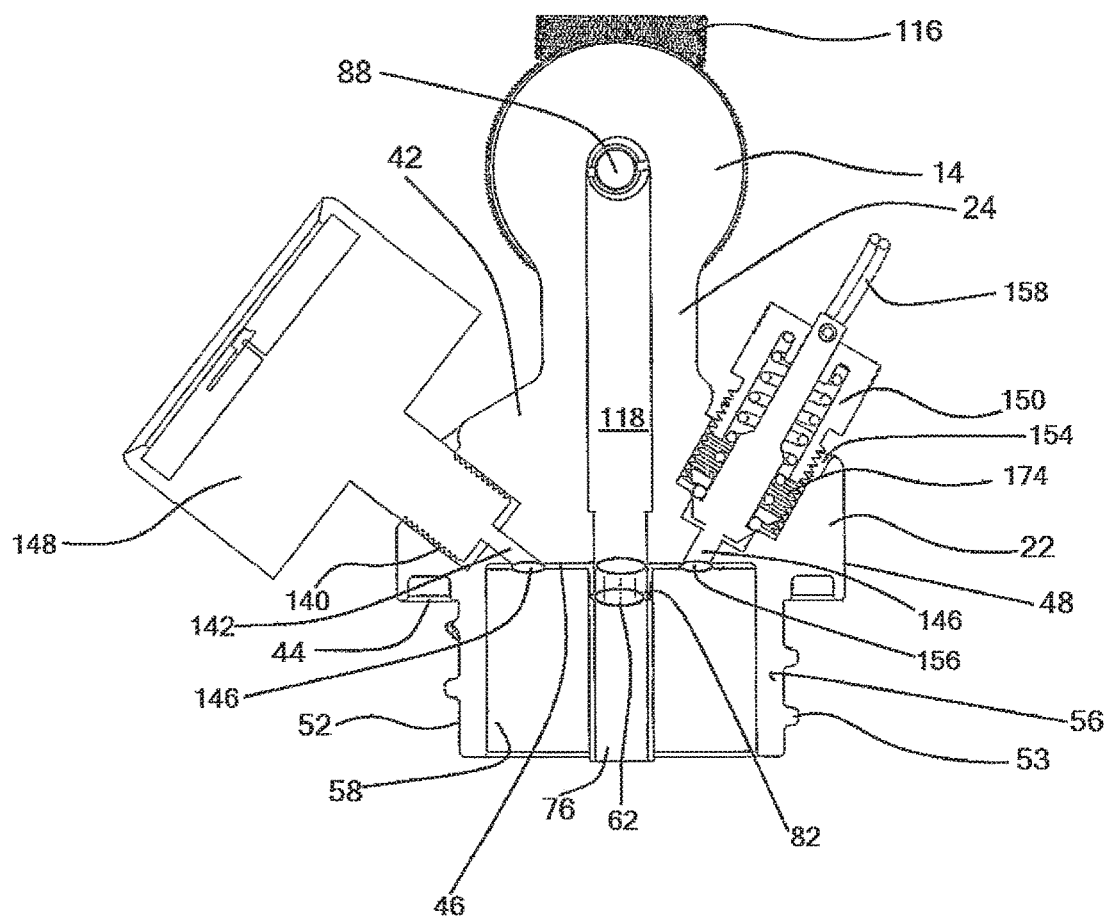
FIG. 13 illustrates an isometric view of a coupler half, illustrating a gas pressure gauge half and a gas pressure relief valve half releasably attached to the coupler half, according to one embodiment of the present disclosure.
Figure 14:
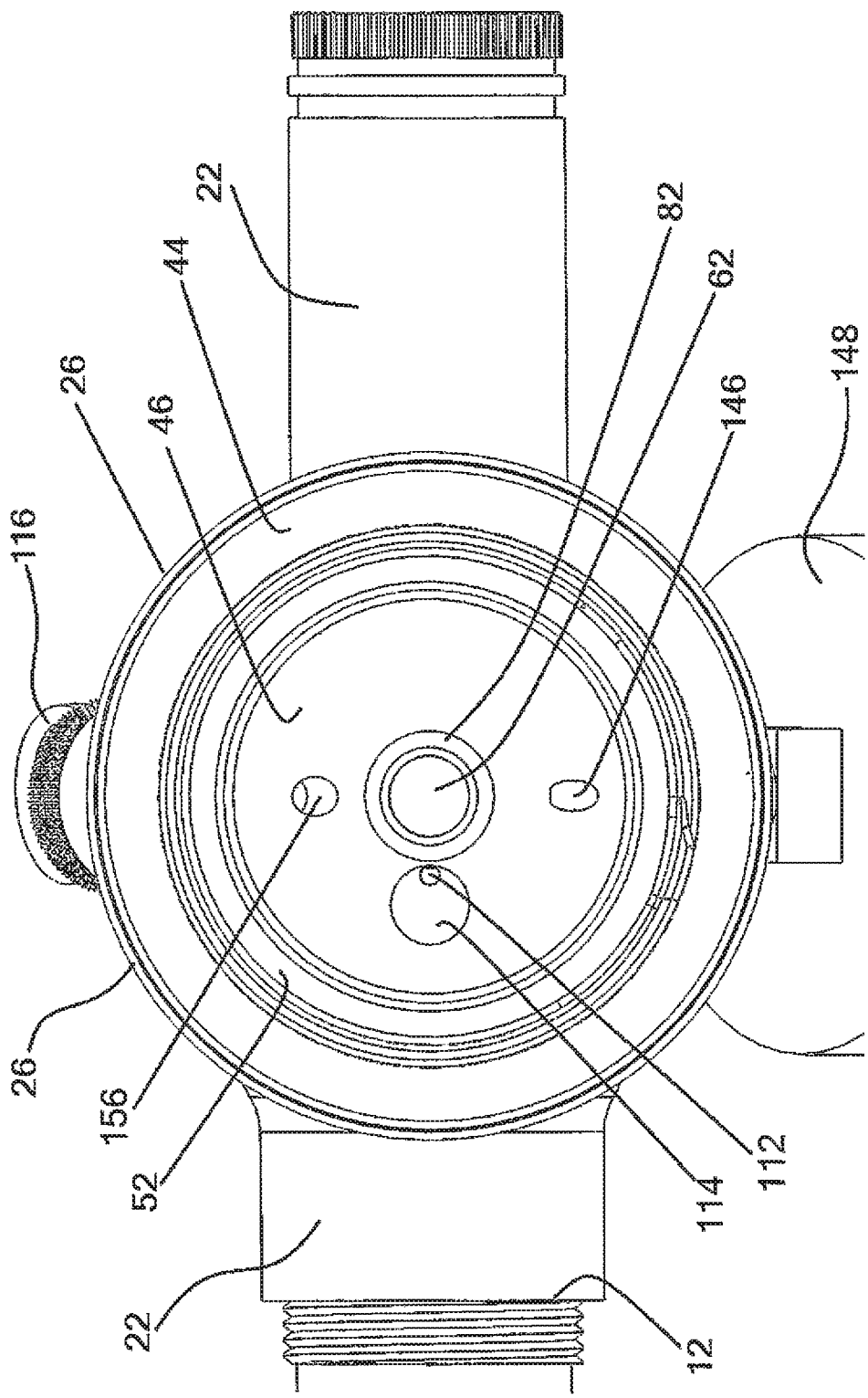
FIG. 14 is a perspective view of the bottom of a cap of the coupler, according to one embodiment of the present disclosure.

Referring to FIGS. 1, 3-4 and 7, and with more particularity FIGS. 13-14, the coupler 20 is configured with a gas pressure gauge 148. In the depicted embodiment, a gas pressure aperture 146 having threads integrally machined within a forward portion of the cap 26 is adapted and operable for releasably threadably attaching a gas pressure gauge 148 via an attachment means.

A second channel of the plurality of channels is a gas pressure channel 142 integrally machined within the cap 26 extending from a caudal end of the gas pressure aperture 146 to a gas pressure gauge port 146, as shown in FIG. 14 integrally machined within the inner sole 46 of the cap 26, wherein the gas pressure channel 132 is adapted for enabling transmission of a gas pressure from within the vessel 60 through the gas pressure gauge port 146 and through the gas pressure channel 132 for measuring by the gas pressure gauge 48.

In the depicted embodiment of the disclosure, the gas pressure aperture 140 includes a seated threaded opening in a forward portion of the cap 26 to releasably attach a $CO_2$ gas pressure gauge 148. In another embodiment of the disclosure, the gas pressure gauge 148 is a $N_2$ gas pressure gauge. In another embodiment of the disclosure, the gas pressure gauge 148 is a $N_2/CO_2$ double gas pressure gauge 148.

The gas pressure channel 142 extends from the caudal end of the gas pressure aperture 140 therethrough the cap 26 to the gas pressure gauge port 146 as shown in FIG. 14 integrally machined within the inner sole 46 of the cap 26, wherein the gas pressure gauge port 146 has an opening fluidly communicable with the interior of the vessel 60 such that the gas pressure gauge 148 displays the gas pressure within the vessel 60.

In the exemplary embodiment of the present invention, the coupler 20, also, includes a gas pressure relief valve 150. A gas pressure relief valve aperture 154 having threads integrally machined within a rearward portion of the cap 26 is adapted and operable for releasably attaching the gas pressure relief valve 150 via an attachment means for enabling one-directional release of a gas composition externally from within the vessel 50, wherein an activation component 158 operatively attached to the gas pressure relief valve 150 is activated upon exceeding a predetermined gas pressure level within the vessel 60.

Referring to FIGS. 2-4, and 6 and with more particularity FIGS. 13-14, the coupler 20 is, also, configured with a gas pressure relief valve 150. A third channel of the plurality of channels is the gas pressure relief valve channel 146 integrally machined within the rearward portion of the cap 26 extending from a base end of the gas pressure relief valve aperture 154 to a gas pressure relief port 156 within the inner sole 46 of the cap 26, wherein the gas pressure relief valve channel 146 is adapted for enabling transmission of the one-directional release of gas composition externally from within the vessel 60 when needed through the gas pressure relief port 156 through the gas pressure relief valve channel 146 and through the gas pressure relief valve 150.

In the exemplary embodiment, the gas pressure relief valve aperture 154 includes threads integrally machined into the rearward portion of the cap 26 of the coupler 20 mateable with threads of the gas pressure relief valve 150 for enabling releasably attaching the gas pressure relief valve 150 and ensuring that the gas pressure relief valve 150 does not inadvertently become disengaged from the gas pressure relief valve aperture 154.

As depicted in FIG. 13-14, the gas pressure relief valve channel 146 integrally machined within the cap 26 extends from a caudal end of the gas pressure relief valve aperture 154 terminating at a gas pressure relief port 156 at the inner sole of the cap 26. The gas pressure relief port 156 is fluidly communicative with the head space 67 of the vessel 60.

The gas pressure relief valve 150, therefore, relieves the pressure within the vessel 60 by expelling excess gas composition or gas composition bi-products from the interior 64 of the vessel 60. Accordingly, the gas pressure relief valve 150 is operable at a predetermined gas pressure and can be activated to open to vent excess gas composition from inside the vessel 60, and accordingly, lowering the pressure within the vessel 60.

In one embodiment of the present disclosure, the gas pressure relief valve 150 is preset such that the gas pressure relief valve 150 automatically becomes unseated when a specified threshold gas pressure level is reached within the vessel 60. In an embodiment of the present disclosure, the gas pressure relief valve 150 is automatically operable such that when a gas pressure is reached to include a range including about 7 psi to 60 psi, wherein the gas pressure relief valve 150 is adapted to maintain an internal pressure within the vessel 60 within a pre-determined range of about 7 psi-60 psi. In another embodiment of the present disclosure, the gas pressure relief valve 150 is adapted and automatically operable to maintain an internal pressure within the vessel 60 within a pre-determined range of about 17 psi-60 psi. In another embodiment of the present disclosure, the gas pressure relief valve 150 is adapted and automatically operable to maintain an internal pressure within the vessel 60 within a pre-determined range of about 0 psi-60 psi.

In another embodiment of the present disclosure the gas pressure relief valve 150 is manually operated by the user pulling on an activation component 158 a ring on the cap of the gas pressure relief valve 150 to cause unseating of the gas pressure relief valve 150 and, accordingly, the gas composition bi-products are expelled from the interior of the vessel 60. By pressing back down on the activation component 158 the gas pressure relief valve 150 is reseated.

With particular reference to FIGS. 8-11 and 15, a fourth channel of the plurality of channels is a fluid delivery channel 118 integrally machined within the coupler 20 having a at least one right angle bend, the fluid delivery channel 118 has a primary opening 124 and a terminal opening 126, the primary opening 124 is commensurate with the bore hole 62 centrally disposed within the cap 26, and the terminal opening 126 commensurate with the anterior opening 38 of the tap head 22. The fluid delivery channel 118 includes a fluid delivery inlet runner 128 fluidly communicable to a fluid delivery outlet runner 130 adapted and operable for the transmission of a flow of the fluid from within the vessel 60 and upstream to a nozzle 84.

In the exemplary embodiment of the present disclosure, the fluid delivery channel 118 is an inverted L-shape, wherein the fluid delivery inlet runner 128 defines a vertical portion of the inverted L-shape passing from the bore hole 62 therethrough a centroidal portion of the cap 26, the shank 24, and the tap head 22, and the fluid delivery outlet runner 130 defines a horizontal portion of the inverted L-shape passing through a central portion of the tap head 22 along the x-axis and terminating at the nozzle opening 86.

In an embodiment of the present disclosure, the fluid delivery outlet runner 130 is a converging-diverging channel, the converging-diverging channel adapted and operable for regulating the transmission of the flow of the fluid during dispensing of the fluid externally from within the vessel 60. In another embodiment of the present disclosure, the fluid delivery outlet runner 130 is a horizontal venturi flow meter adapted and operable for regulating the transmission of the fluid externally from within the vessel 60. In another embodiment of the present disclosure, the delivery outlet runner 130 is tapered configured and operable for regulating the transmission of the fluid externally from within the vessel 60.

As depicted in FIG. 8, the fluid pressurization and dispensing system includes a fluid delivery tube 76 operatively connected to the hose barb 82 circumventing the bore hole 62 such that the fluid delivery tube 76 is provide in the interior 64 of the vessel 60.

The fluid delivery tube 76 is adapted for enabling transmission of the fluid 186 contained from within the vessel 60 through to the fluid delivery channel 118, wherein the fluid delivery tube 76 includes a first end 78 and a second end 80 having a length ($L^4$) therebetween and a cross-diameter ($CD^4$), wherein the first end 78 having a first opening is operatively connected to the hose barb 82 circumventing the bore hole 62, and the second end 80 having a second opening is provided immersed therein the fluid 186 contained within the vessel 60.

The fluid delivery tube 76 is manufactured from a food-grade tubing material selected from the group comprising of: a polyethylene tubing, a barrier tubing, a polymer tubing, and a stainless steel tubing.

In the exemplary embodiment, the fluid pressurization and dispensing system 10 includes a faucet 88 operatively connected to the nozzle 84 via an attachment means, wherein the faucet 88 is adapted for receiving the fluid 186 contents from the fluid delivery channel 118 and adapted for dispensing the fluid 186 contents externally from within the vessel 60. The faucet 88 is operatively connected to the coupler 20 to enable adequate and proper flow of the fluid 186 contents externally from within the vessel 60 into a receptacle for consumption of the fluid 186 by the user.

Referring back to FIGS. 6-8 and 10 the tap head 22 defines the top cylindrical portion of the coupler 20. At the anterior end 12 of the tap head 22 the nozzle 84 is configured and operable to releasably attach the faucet 88 configured to allow a user to regulate flow of the fluid 186 through the fluid dispensing tube 70. The nozzle 84 includes the nozzle opening 86 commensurate with the anterior opening 38 of the tap head 22 which is commensurate with the terminal opening 126 of the fluid delivery tube 76 such that the fluid 186 held in the vessel 62 passes through the nozzle 84 into the opening of the faucet 88 and, subsequently, passes externally from the vessel 60 and, preferably, into a fluid receptacle, for example, a liquid beverage receptacle including glassware, a glass, a beer glass, or wine glass, a mug, and the like.

The faucet 88 can include a standard faucet. The faucet 88 can be selected from the group of beer faucets comprising a standard, a ventless with shaft, a ventless without shaft, a nitro-faucet, a spring loaded cam-actuated, and a roto-faucet. The faucet 88 can, also, be selected from the group comprising a European faucet, and flow control faucet. In an embodiment of the present disclosure, the coupler 20 will include a first faucet adaptor (not shown) compatible to releasably attach the European faucet, and a second faucet adaptor (not shown) compatible to releasably attach the flow control faucet to the nozzle 84.

In addition, the fluid 186 can be a nitro-beer which can be dispensed implementing a faucet 88 which is a stout including a removable restrictor plate 172 having perforations 173 and operable to slow down the speed of the pour and ensure a fuller head. In an exemplary embodiment of the present disclosure, the nozzle 84 is configured and operable to releasably attach a stout faucet including a removable restrictor plate 172 having perforations 173 and operable to slow down the speed of the pour. The faucet 88 can include indicia provided thereon representing the type of fluid contained in the vessel 62. I The gas source may be a compressed gas source such as a commercially available pre-pressurized cartridge of carbon dioxide ($CO_2$), nitrogen ($N_2$), $CO_2$ and $N_2$ blend, or argon, or any gas capable of being contained in a small quantity. The pre-pressurized gas composition cartridges can be refillable or disposable pre-pressurized gas composition cartridges 94. In an embodiment of the present disclosure, the pressurized gas composition cartridge 94 comprises a pre-pressurized CO2 gas composition cartridge 94 that is disposable. In another embodiment of the present disclosure, the pressurized gas composition cartridge 94 comprises a pre-pressurized CO2 gas composition cartridge 94 that is disposable.

In an embodiment of the present disclosure, the gas injection aperture 96 can include an integrally machined threaded female opening adapted and operable for releasably attaching a male threaded opening of a pre-pressurized gas composition cartridge 94. In another embodiment, the gas injection aperture 96 can include an integrally machined threaded male opening adapted and operable for releasably attaching a threaded female opening of a pre-pressurized gas composition cartridge 94.

In the exemplary embodiment of the present invention, the gas injection aperture 96 is compatible with pre-pressurized gas compositions cartridges 94 including one or more of the following: 6 grams, 8 grams, 12 grams, 16 grams, 25 grams, and 33 grams. The pressurized gas composition cartridge 94 can be any one of the pressurized gas composition cartridges selected from the group of carbon dioxide ($CO_2$), nitrogen ($N_2$), $CO_2$ and $N_2$ blend, or argon, in 6 grams, 8 grams, 12 grams, 16 grams, 25 grams, and 33 grams. The pressurized gas cartridges can include gas compositions of $CO_2$ composition alone, or a combination of $N_2$ and $CO_2$ gas composition blend, or more particularly a $N_2$ and $CO_2$ gas composition blend having 70-75% $N_2$; 25-30% $CO_2$. In an embodiment of the present disclosure the gas composition cartridge includes a 25% $CO_2$ and 75% $N_2$ customized gas composition cartridge 94 which is implemented for fluids 186 that comprise nitro-beers.

In the exemplary embodiment of the present disclosure, the pressurized gas composition cartridges 94 are pre-pressurized gas composition cartridges 94. In another embodiment of the present invention, pressurized gas composition cartridges 94 can be refillable gas composition cartridges 94.

The pressurized gas composition cartridge 94 can comprise one or more of the following: a disposable pre-pressurized $N_2$ and $CO_2$ blend gas composition cartridge, a disposable pre-pressurized $N_2$ gas composition cartridge, a disposable pre-pressurized $CO_2$ gas composition cartridge, a disposable pre-pressurized argon gas composition cartridge. The pressurized gas composition cartridge can comprise one or more of the following: a refillable pre-pressurized 70% $N_2$ and 30% $CO_2$ blend gas composition cartridge, a refillable pre-pressurized 75% $N_2$ and 25-30% $CO_2$ blend gas composition cartridge.

For standard beer the pressurized gas composition cartridge 94 can include 60% $CO_2$/40% $N_2$; 70% $CO_2$/30% $N_2$; 75% $CO_2$/25% $N_2$. For a nitro beer the pressurized gas composition cartridge 94 includes a gas composition including a $N_2$ and $CO_2$ gas composition having 70-75% $N_2$ and 25-30% $CO_2$. In another embodiment of the present invention, the pressurized gas cartridge 94 includes an argon gas composition. The pressurized gas composition cartridges 94 are colored coded to indicate the type of gas composition contained therein.

The pre-pressurized gas composition cartridges 94 are color coded such that a designated color identifies a type of fluid 186 contained within the vessel 60.

In addition, the pressurized gas composition cartridges 94 can include flavors to be implemented into the fluid 186 contained in the vessel 60 adapted for adding to the flavor of the fluid 60 contained in the vessel 60. In addition, the pressurized gas composition cartridge 94 can include a gas to clean out the integrally machined channels within the coupler 20 and to clean the interior of the vessel 60.

In another embodiment of the present invention, the coupler 20 includes a plurality of gas injection apertures 96 so that each one of a plurality of pressurized gas composition cartridges 94 can be releasably attached therein to each one of a corresponding gas injection apertures 96, simultaneously.

In another embodiment of the present invention, the tap head 22 of the coupler 22 comprises at least two gas injection apertures 96 integrally machined within the tap head 22 adapted and operable for simultaneous releasably attaching of two individual pressurized gas composition cartridges 94 simultaneously to the coupler 20. The at least two gas injection apertures 96 includes each of two gas injection apertures 96 integrally machined within the coupler 20 for enabling releasably attaching simultaneously a first pre-pressurized gas composition cartridge 94 having a female attachment means and releasably attaching a second pre-pressurized gas composition cartridge 94 having a male attachment means adapted for the transmission of a blended flow of gas composition into the vessel 60.

In another embodiment of the present disclosure, the coupler 20 includes two-gas injection apertures 96 wherein one of the gas injection apertures 96 includes a threaded male attachment means including a fistula 92 adapted and operable to releasably attach a female attachment means of a pressurized gas composition cartridge 94, and the second gas injection aperture 96 includes a threaded female attachment means including a fistula 92 adapted to and operable to releasably attach a male attachment means of a pressurized gas composition cartridge 94.

A gas check valve (not shown) can be disposed between the two gas injection apertures 96 configured and operable to shut one gas flow channel such that a second gas flow channel is open to receive the flow of gas from one of the pressurized gas composition cartridges 94.

As depicted with more detail in FIGS. 8-12 and 14, the fluid pressurization and delivery system 10 includes the gas pressure regulator 90 positioned within the seat 100 of the coupler 20, as shown in FIG. 6 and FIGS. 10-14. The flow of the gas composition exiting the pressurized gas composition cartridge 94 and passing into the head space 67 above the fluid contained within the vessel 60 is regulated by the gas pressure regulator 96 configured and operable to regulate the flow of gas in one direction.

The seat 100 is integrally machined within the tap head 22 extending from the posterior opening 40 of the tap head 22 and, accordingly, operatively fluidly communicable with the posterior opening of the tap head 22 of the coupler 20 at the posterior end 14. The seat 100 is configured for enabling for seating of the gas pressure regulator 90 within the tap head 22 such that the base end 206 of the gas pressure regulator 90 is proximate to the upper gas flow channel 106 for enabling fluid communication between the pressurized gas composition cartridge 94 and the gas pressure regulator chamber 98 through the gas flow channel 104.

The gas pressure regulator 90 includes a valve 20, a rotary actuator 116, two o-rings 201 and 202; a bonnet 212, a disc 204, a non-porous membrane 97, a base 206, and a spring 210, and the gas pressure chamber 98.

Referring to FIGS. 9-12 sectional views of the gas pressure regulator 90 is shown. The gas pressure regulator 96 is releasably inserted into the seat 100 and threadably attached to the posterior opening 40 via a retainer portion 214 of the gas pressure regulator 90. A first o-ring 201 is provided at the base end 204$^2$ of the disc 204 and a second o-ring 202 is provided at a lip 216 of the disc 216 configured to ensure a leak-proof barrier to the gas pressure chamber 98 for sealing against any back-flow of the gas composition.

The non-porous membrane 97 is generally a circumpherential non-porous membrane disposed transversely between the bonnet 212 and the disc 204. The non-porous membrane 97 is adapted for allowing a non-porous seal between the gas pressure regulator chamber 98 and the bonnet 212 operable to provide a leak-proof barrier to the gas pressure chamber 98 and operable to seal against any back-flow of the gas composition.

The non-porous membrane 97 transversely separates the gas pressure regulator 90 into a right side portion and a left side portion of the gas pressure regulator. The front side $97^1$ of the non-porous membrane 97, the stem 117, and the bonnet 212 constitute the right side portion of the gas pressure regulator 90. The rear side $97^1$ of the non-porous membrane 97, the disc 204, the two-o rings 201 and 202, the spring 210 and the gas pressure chamber 98 constitute the left side the gas pressure regulator 98.

The non-porous membrane 97 is preferably manufactured with nitrile rubber.

Dependent from the non-porous membrane 97 is the disc 204 which extends axially through the gas pressure chamber 98 and is configured to move linearly inside the gas pressure chamber 98 in response to the linear movement of the non-porous membrane 97. The disc 204 includes a front end $204^1$ and a back end $204^2$. The back end $204^2$ of the disc 204 is configured and operable to seal against the base of the seat 208 of the gas regulator chamber 98. The first o-ring 201 is positioned against the back end $204^2$ of the disc 204 to provide a leak-proof seal against back-flow of the flow of gas composition as it enters the gas pressure regulator chamber 98. In addition, a second o-ring 202 is positioned against a lip 216 of the disc 204 to ensure additional protection against back-flow of the gas composition.

Referring to FIGS. 9-12 illustrating the embodiment of the gas pressure regulator 90, more particularly, a rotary actuator 116 is operatively connected to the gas pressure regulator 90 at the posterior opening 40 of the tap head 22. The rotary actuator 116 allows a user of the fluid pressurization and dispensing system 10 to inject a regulated amount of gas composition from the gas composition cartridge 94 into the vessel 60 to pre-pressurize, pressurize, or re-pressurize the fluid 186 contents contained within the vessel 60.

In the depicted embodiment of the present disclosure, the gas pressure regulator 90 is seated within the tap head 22 extending from the posterior opening 40 of the coupler 20 wherein the gas pressure regulator 90 is configured and operable to provide an adjustable gas pressure regulator valve implementation via the rotary actuator 116. The valve body 200 includes a stem 117 which includes external threads which are threadably compatible with the internal threads of the rotary actuator 116 adapted for enabling rotation of the rotary actuator 116 towards one direction to a closed position and rotated towards the opposite direction to an open position to allow for the passage of the gas flow into the gas regulator chamber 98 and to exit the gas flow chamber 98. A central portion of the seating 208 defines the gas pressure chamber 98 configured as a hollow spaced section of the seat 100 and operable to provide for the passage of a flow of pressurized gas received therein from the pressurized gas composition cartridge 94 via the upper gas flow channel 106 and into the vessel 60 via the lower gas flow channel 108.

In the exemplary embodiment, the upper gas flow channel 106 and the lower gas flow channel 108 of the gas pressure regulator 108 are in fluid communication with the gas pressure chamber 98. The upper gas flow channel 106 provides a passage for a flow of pressurized gas from the pressurized gas composition cartridge 94 into the gas pressure chamber 98 and is in fluid communication with the gas pressure chamber 98. The lower gas pressure channel 108 is in fluid communication with the gas pressure chamber 98 as depicted in FIGS. 8-12. The upper gas flow channel 106 integrally machined within the tap head 22 provides a passage therethrough for the flow of gas composition from the pressurized gas composition cartridge 94 passing through a portion of the tap head 22 through to the gas pressure regulator 90, and the lower gas flow channel 108 provides a passage therethrough for the flow of gas composition passing from the gas pressure regulator chamber 98 through a portion of the tap head 22, a portion of the shank 24 and through the inner sole 46 of the cap 26 to the gas inlet port 112 which is adapted for enabling the transmission of the flow of gas composition into the interior 64 of the vessel 60, wherein the gas inlet port 112 is fluidly communicable with the interior of the vessel 60 for enabling for the purging of the flow of gas composition into the vessel 60.

When the fluid 186 contained in the vessel 60 is a carbonated fluid, for example, beer, or nitro-beer, or soda, the fluid requires pressurization within the vessel in order to maintain carbonation and freshness of the carbonated fluid. In one aspect, accordingly, to the present disclosure the rotary actuator 116 can be rotated to an open position to inject a regulated volume of the flow of gas composition into the vessel 60 through the mechanism of the gas pressure regulator 90 to transmit an initial flow of gas composition from the gas pressure composition cartridge 94 into an empty vessel 60 previous to being filled with the fluid 186 contents to displace any oxygen gas source, for enabling pre-pressurization of the vessel.

In another aspect, the user can turn the rotary actuator 116 to an open position to re-pressurize the fluid contents within the vessel 60 when an excess gas composition of bi-products has been expelled through the gas pressure relief valve 150 and, accordingly, maintaining the pressurization within in the vessel 60 and the freshness of the fluid 186 contents, for example, beer, nitro-beer, soda, within the vessel 60.

The rotary actuator 116 is releasably threadably attached to exterior threads of the stem 117 of the gas pressure regulator 90. Depending from the stem 117 is the bonnet 212. When the rotary actuator 116 is turned counter-clockwise to a closed position the disc 204 is sealed against the base of the seat 208. The spring 210 for spring-loading is configured to allow control to laterally move the disc 204. The spring is implemented to keep the disc 204 sealed against the seat 208 and, also, allow the rotary actuator 116 to direct the spring 210 to allow the disc 204 adapted to move laterally away from the seat 208 unseating the two-o rings 201 and 201 for enabling the flow of gas composition to enter into the gas pressure regulator chamber 98 as described in more detail immediately below. The adjustment of the spring 210 pressure depends upon the rotation of the rotary actuator clockwise or counterclockwise causing the spring 210 to tighten or loosen. In the exemplary embodiment of the present invention, the release gas pressure is variable from 0-60 psi, 7-60 psi, and 17-60 psi. The spring 210 is manufactured from stainless steel.

When the pressurized gas composition cartridge 94 is releasably attached to the gas injection aperture 96 and as the rotary actuator 116 is turned a pre-selected degree clockwise the bonnet 212 moves laterally and advances against the front side $97^1$ of the non-porous membrane 97. Accordingly, the rear side $97^2$ of the non-porous membrane 97 advances against a front end $204^1$ of the disc 204 causing the back end $204^2$ of the disc 204 to deflect the first o-ring 201 accordingly unseating the rear end of the disc $204^2$ from the seat 208 and accordingly releasing the seal against the base of the gas pressure chamber 98 for enabling the release of the flow of gas composition into the gas pressure chamber 98. In addition, the seal between the second o-ring 202 and the disc 208 is unseated. While the disc 208 is unseated, the pressurized gas composition initiating from the pressurized gas composition cartridge 94 is allowed to pass through the upper gas flow channel 106 into the gas pressure regulator chamber 98 and to pass from the gas pressure regulator chamber 98 into the lower gas flow channel 108 and exit through the gas inlet port 112 within the inner sole 46 of the cap 26 and into the interior 64 of the vessel 60.

The rotary actuator 116 is manually adjusted by the user until the desired regulated pressure is obtained. Insignia can be positioned on the rotary actuator 116 to identify the amount of regulated pressure released into the gas pressure chamber 98.

In another embodiment of the present invention the gas pressure regulator 90 can be autonomous and self-regulated.

In closer inspection, in the depicted embodiments in FIGS. 10-12, the gas flow channel 104 includes the upper gas flow channel 106 and the lower gas flow channel 108 integrally machined into the coupler 20. The upper gas flow channel 106 has at least one bend configured and operable to maintain a flow of gas composition under high pressure, and the lower hollow gas channel 108 having at least one bend having a right angle in shape is configured and operable to maintain a flow of gas composition under a regulated pressure. The gas flow channel 104 is machined into the solid interior of the coupler 20, and, more particularly, the upper gas flow channel 106 is integrally machined within the tap head 22 having a v-shape passes through the tap head 22 of the coupler 20, and the lower gas flow channel 106 having an inverted L-shape is integrally machined passes through the tap head 22, the shank 24, and the cap 26 terminating at the gas inlet port 112 adapted for enabling the upper gas flow channel 106 for passing through the tap head 22 of the coupler 20, and the second bend of the lower gas flow channel 108 passes through the tap head 22, the shank 24, and the cap 24 of the coupler 20.

The v-shaped bend in the upper gas flow channel 106 and the inverted L-shape of the lower gas flow channel 108 is influential in the rate of the flow of the gas composition as it passes through the gas flow channel 104 of the coupler 20 as the gas composition flow is transmitting therethrough to the gas inlet port 112. In the exemplary embodiment of the present invention, the bend in the upper gas flow channel 106 is v-shaped. In another embodiment, the upper gas flow channel 106 is spiral shaped. In another embodiment of the present invention, the upper gas flow 106 channel is linear in shape. In the exemplary embodiment of the present invention, the bend in the lower gas flow channel 108 includes a right angle. In another embodiment of the present disclosure, the lower gas flow channel 108 includes a spiral shape having a right angle bend.

The upper gas flow channel 106 transversely extends from a caudal end of the gas injection aperture 110 to the gas pressure regulator chamber 98 wherein the upper gas flow channel is fluidly communicable with the pressurized gas composition cartridge for enabling transmission of the flow of gas composition from the pressurized gas composition cartridge 98 and into the gas regulator chamber 98.

The lower gas flow channel 108 is fluidly communicable to the gas pressure regulator chamber, wherein the lower gas flow channel extends linearly from the gas pressure regulator chamber 98 therethrough a portion of the tap head 22 and continues until it bends at the right angle to extend downward towards the shaft 24 and therethrough extends vertically to within the inner sole 46 of the cap 26 where the lower gas flow channel 108 terminates at the gas inlet port 112 fluidly communicable with the headspace 67 of the vessel 60 for enabling the transmission of the gas flow composition into the interior 64 vessel 60.

In an exemplary embodiment of the present disclosure, the length of the gas pressure relief valve aperture 154 includes a length which is adapted to releasably threadably receive a threadable tail 151 of a variable gas relief valve 150. The length L of the seated opening provides a machined threaded channel in which the tail 151 of the gas pressure relief valve 150 can be rotated in or out causing a variable amount of gas composition under pressure to be vented therethrough the gas pressure relief valve 150. Accordingly, rotating the gas pressure relief valve 150 within the gas pressure relief aperture 154 causes a designated length of the tail 151 of the gas pressure relief valve 150 to be reached within the gas pressure relief aperture 154. Indicia printed on the tail 151 identifies a specific preset psi which corresponds to a specific length of the tail 51 and, accordingly, causes the gas pressure relief valve to automatically open as a pre-set psi level, for example, at about 0-60 psi, at about 17-60 psi, at about 17-60 psi, or at about any one of a pre-selected psi level is achieved.

The gas pressure relief valve 150 can be selected from a variety of gas pressure relief valves having a variety of tail lengths and a variety of components.

In an embodiment of the present invention, the gas pressure relief valve 150 includes an activation component 158. The activation component is a valve cap with a ring 158. The activation component 158 is urged upward as the pressure increases in the interior of the vessel and a flow of gas passes through the gas pressure inlet port 156 and therethrough the gas pressure relief aperture 154 out, accordingly, out to the environment. The gas pressure relief valve 150 is a one-way pressure valve preventing the purge of gas from reentering the interior of the vessel 60. The gas pressure relief valve 150 is a one way valve to purge the gas by-products as the liquid oxidizes within the vessel 60. To replace the purged gas by-products with a new flow of gas composition the rotary actuator 116 is rotated a pre-selected degree causing a pre-selected volume of gas composition to be purged into the interior headspace 67 of the vessel 60 allowing the liquid beverage 186 to retain its freshness. As noted above, the gas composition can be selected from any one or more of the following: The pressurized gas composition cartridges can include gas compositions of $CO_2$ composition alone, or a combination of $N_2$ and $CO_2$ composition, or more particularly a $N_2$ and $CO_2$ gas composition having 70-75% $N_2$; 25-30% $CO_2$.

The gas pressure relief valve 150 can be selected from a variety of gas pressure relief valves.

Umbrella valves are elastomeric valve components that have an umbrella shape. The elastomeric component is used as a sealing element in backflow prevention in the pressure relief valve permanently configured on the valve cap of the coupler 20. The umbrella valve allows forward flow of the excess gas pressure once the head space gas pressure creates enough force to lift the cylindrical diaphragm from the seat of the umbrella valve such that it will allow excess gas flow at a predetermined pressure in one way forward direction away from the valve and prevent back flow immediately in the backward direction back into the vessel 62.

The gas pressure relief valve 150 in an embodiment of the present disclosure includes an umbrella valve configuration to relieve pressure and reset itself, autonomously. The umbrella gas pressure relief valve includes a seat. The seat is cylindrical and extends upright from the exterior surface of the valve cap in which is inserted a Belleville type spring having an umbrella. The umbrella is forced by the release of excess gas pressure from the vessel 60 and causes the umbrella to pop up into an open position and to reset to a closed position when the gas pressure when the gas pressure returns to a predetermined value. The umbrella valve resets by means of the Belleville type spring such that the umbrella portion lowers against the seat and resets itself when the gas pressure is relieved. The Belleville type spring includes a Belleville spring washer held by an elastomeric hinge operable to open once a predetermined gas pressure is achieved.

Thus the gas pressure relief valve 150 is configured to release excess gas pressure from the head space of the vacuum sealed vessel 60, thereby minimizing the possibility of an explosion or deformation of the vessel 60 due to over-pressurization. In an embodiment of the present invention the umbrella valve is calibrated to open when an internal vessel pressure of from about 0-60 psi is reached, or at about 7-60 psi, at about 17-60 psi is achieved.

In another embodiment of the present disclosure, the gas pressure relief valve 150 is an minivalve umbrella valve releasably attached to the gas pressure relief valve aperture 154 of the cap 26 of the coupler 20. In another embodiment of the present invention, the gas pressure relief valve 150 is a duckbill valve releasably attached to the gas pressure relief valve aperture 154 the cap 26 of the coupler 20. In another embodiment of the present invention, the gas pressure relief valve 150 is an umbrella/duckbill valve releasably attached to the gas pressure relief valve aperture 154 of the cap 26 in the coupler 20.

In another embodiment according to the present disclosure, the gas pressure relief valve 150 is a minivalve that can vary the opening pressure of a standard umbrella valve. The minivalve is commercially available. The umbrella valve uses its elastic material properties and its preloaded convex shape to create the sealing force against the seat and that it uses the central stem to hold the component in place such that the need for the spring, or a central or circumferential disc positioner is overcome.

In another embodiment of the present invention, the Belleville type wherein the shape of the membrane looks like a Belleville spring washer held by an elastomeric hinge in the center. The gas pressure relief valve 150 will open commensurate with a predetermined pressure limit is achieved. A central stem is located downstream of the valve and is held in place by the gas pressure relief valve aperture 154 having mateable threads to that of the stem of the Belleville type valve. This type of valve includes only one gas flow orifice.

Minivalve umbrella valves work with a specific seat design which is releasably attached to the gas pressure relief valve aperture 154 of the cap 26, wherein the gas pressure relief valve aperture 154 is in fluid communication with the gas flow orifice 156 to enable excess gas flow to be released from the vessel 60.

Figure 15:
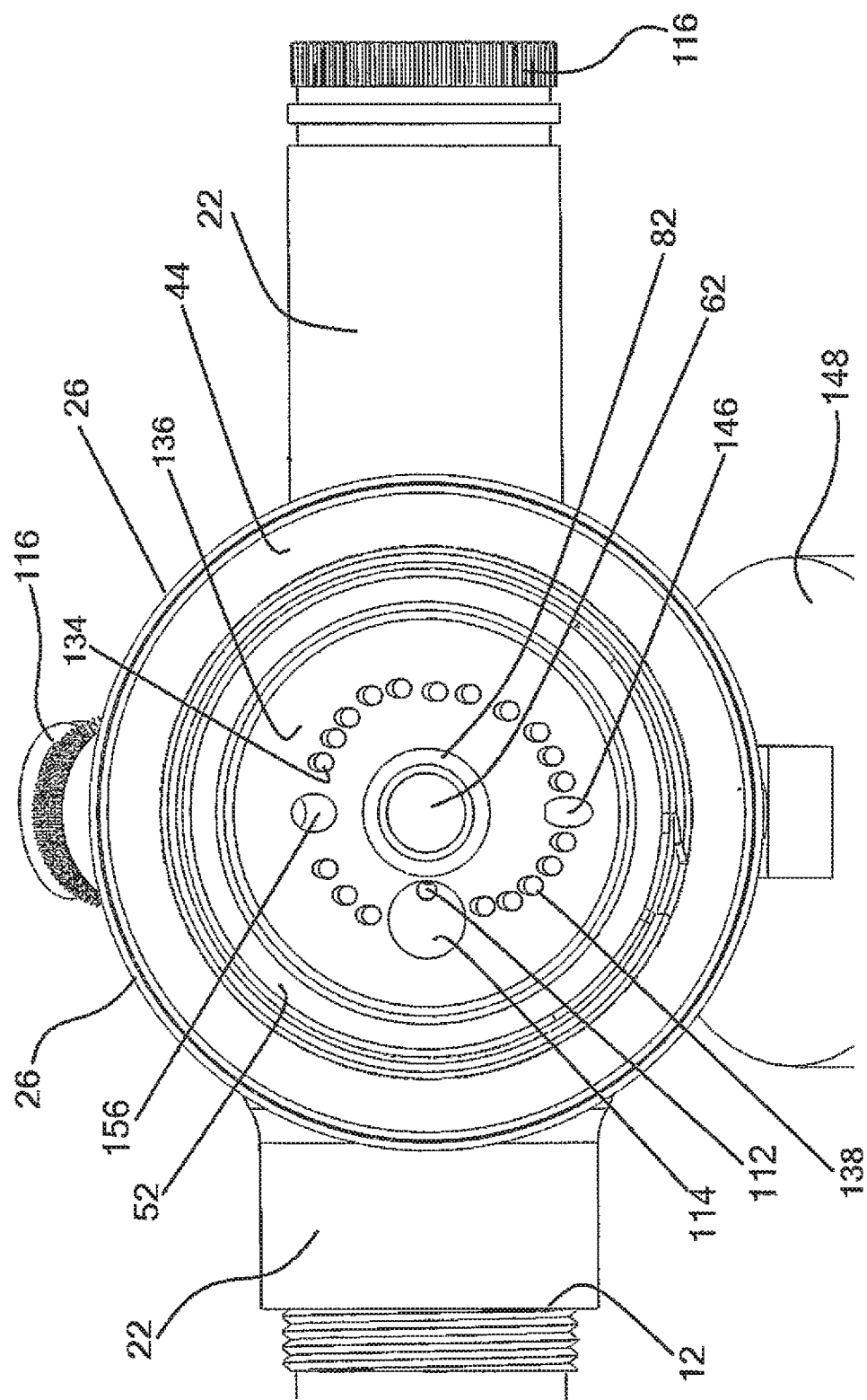
FIG. 15 is a perspective view of the bottom of a cap of a coupler, according to another embodiment of the present disclosure.

Referring to FIG. 15, in another embodiment of the present disclosure, the cap 26 includes an inner sole 46 that is perforated, a perforated inner sole 136. The perforated inner sole 136 comprises a plurality of perforations 138 integrally machined within the inner sole 46, wherein the plurality of perforations 138 are operatively fluidly communicable to the gas inlet port 112. The plurality of perforations 138 are each integrally machined within the inner sole 46 of the cap 26, wherein each of the plurality of perforations 138 includes a pore opening 134 fluidly communicative with the interior of the vessel 60 adapted and operable for enabling increased harmonious transmission of the flow of gas composition from the lower gas flow channel 108 into the interior 64 of the vessel 60 by means of simultaneous purging of the flow of gas composition through the plurality of perforations 138 into the vessel 60.

The perforated inner sole 136 implements the ability of the coupler 20 to provide a gas composition flow to enter the vessel 60 for enabling the gas composition to reach equilibrium rapidly within the vessel 60. The gas flow of gas composition can flow freely and maintain a constant gas composition because the flow path provided by the plurality of perforations 138 has a higher flow capacity than the lower gas flow channel 108 can supply and therefore no restriction occurs between the lower gas flow channel 108 and the interior of the vessel 60.

The perforated inner sole 136, with the median diameter of each of the pores being equal, the purge of the gas composition under pressure into the head space of the vessel 62 can become the dominant factor to control the carbonation of the liquid contained therein and thus the oxygenation of the fluid 186 contained within the vessel 60 can be mitigated either by applying an increase gas composition flow rate by adding a small increase of pressure of gas composition from the pressurized gas composition cartridge 94 regulated by the user by implementing the rotary actuator 116 of the gas pressure regulator 96. Thereby the flow of gas composition purged into the headspace 67 of the vessel 60 provides a consistent flow of gas composition travelling through the plurality of perforations 138 so that carbonation is readily established. Accordingly, the capacity inlet flow capability of the plurality of port openings 134 of the perforations 138 can enable the coupler 20 to produce a consistent gas composition delivery, for example, any one of $CO_2$, $CO_2$ and $N_2$ blend, $N_2$, and argon, into the headspace with greatly diminished system maintenance, which is a special advantage for maintaining freshness of the fluid 186 contained in the vessel 60, for example, a liquid beverage, a volume of beer, a volume of wine, a volume of soda, a volume, of carbonated water, a volume of a carbonated liquid beverage, a volume of a non-carbonated liquid beverage, beer, wine, soda, seltzer, water. The fluid 186 contained in the interior 64 of the vessel 60 can comprise a fluid 186 selected from the group comprising of: a pressurized liquid beverage, a carbonated liquid beverage, and a nitrogenated liquid beverage. In another embodiment of the present disclosure, the fluid 186 can be a gas, for example, argon.

Figure 17:
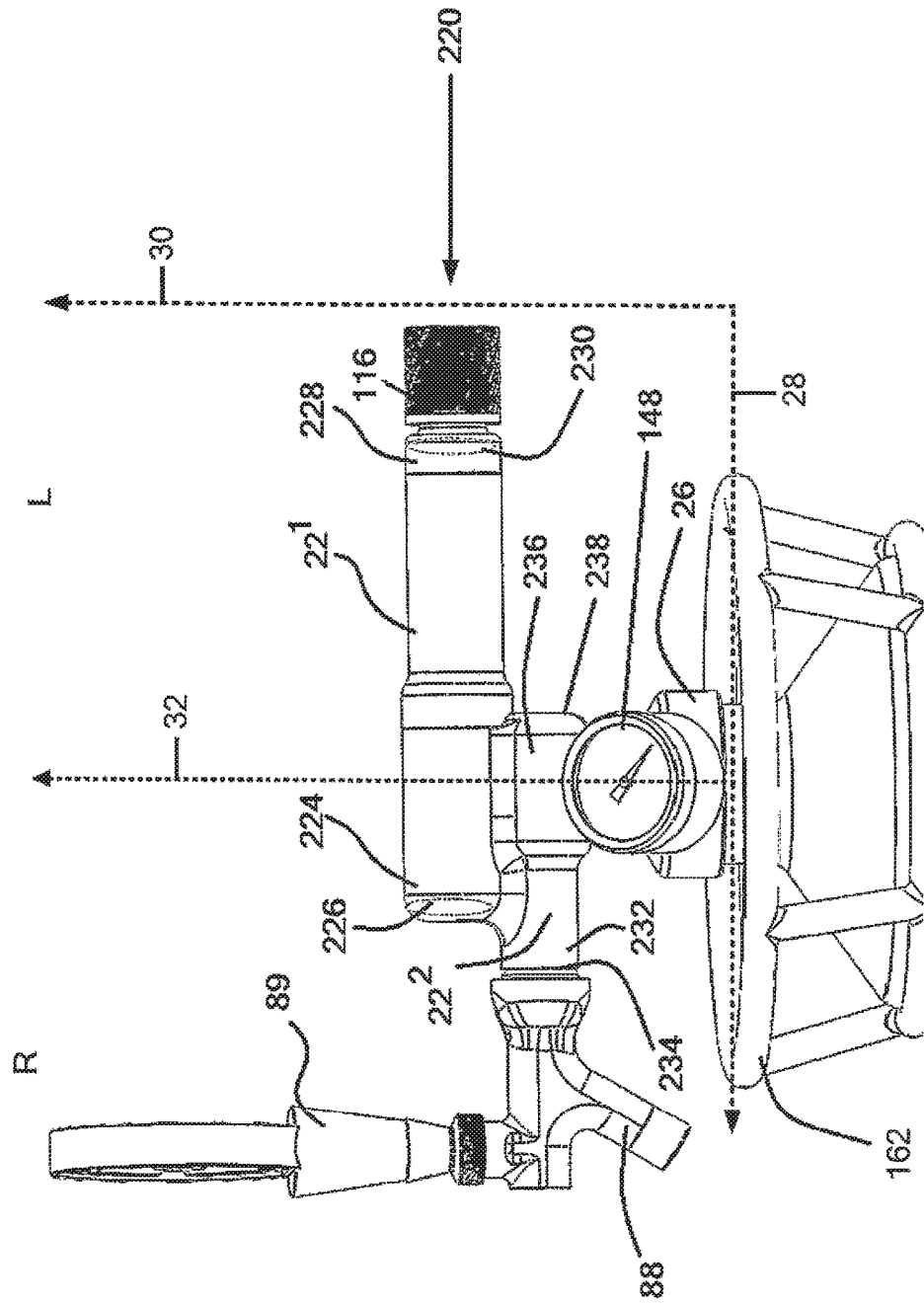
FIG. 17 is an isometric view of a coupler including a bi-level tap head, according to an embodiment of the present disclosure.
Figure 18:
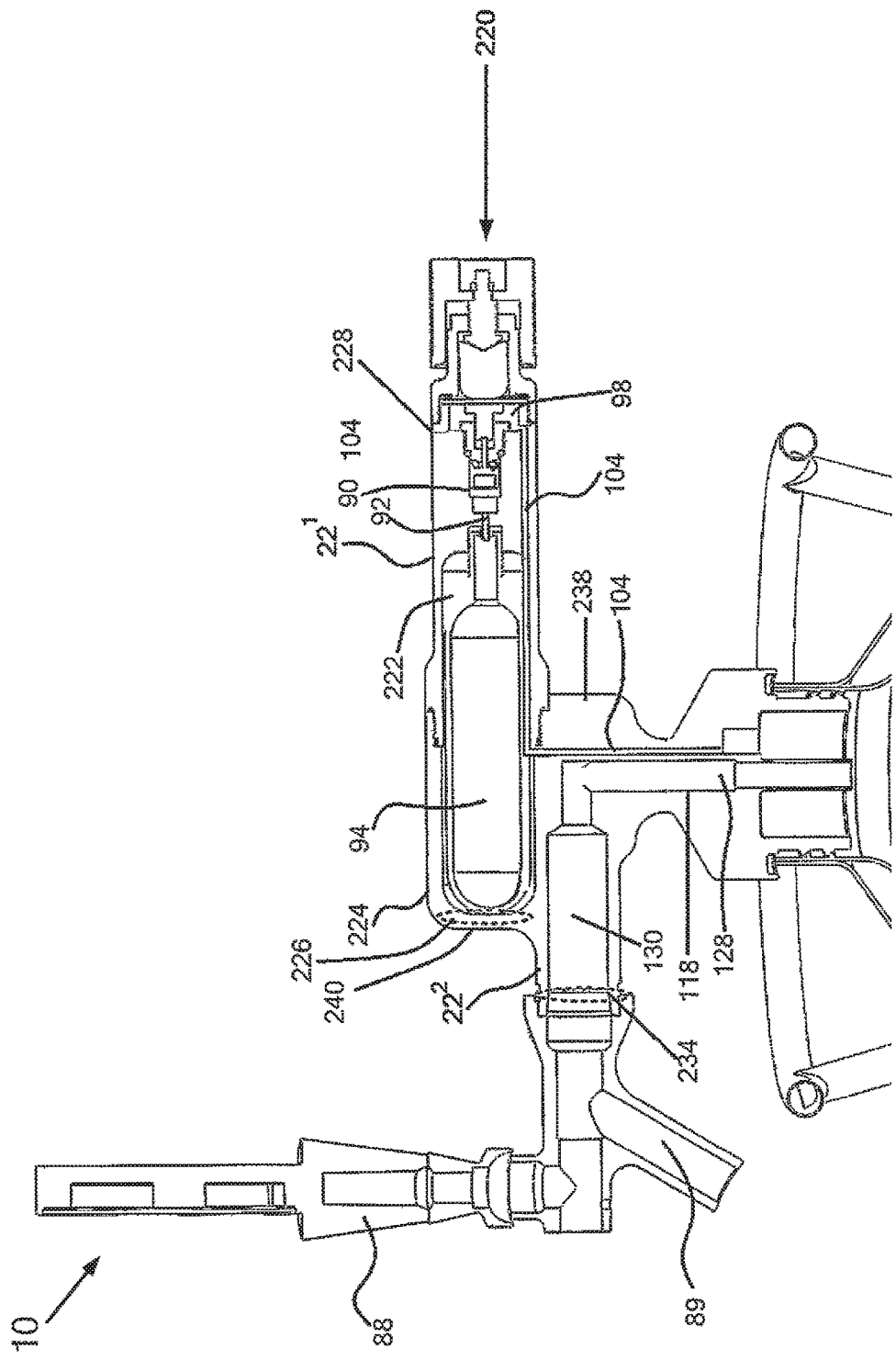
FIG. 18 includes a sectional view of the coupler half including the bi-level tap head half of FIG. 17, according to an embodiment of the present disclosure.
Figure 19:
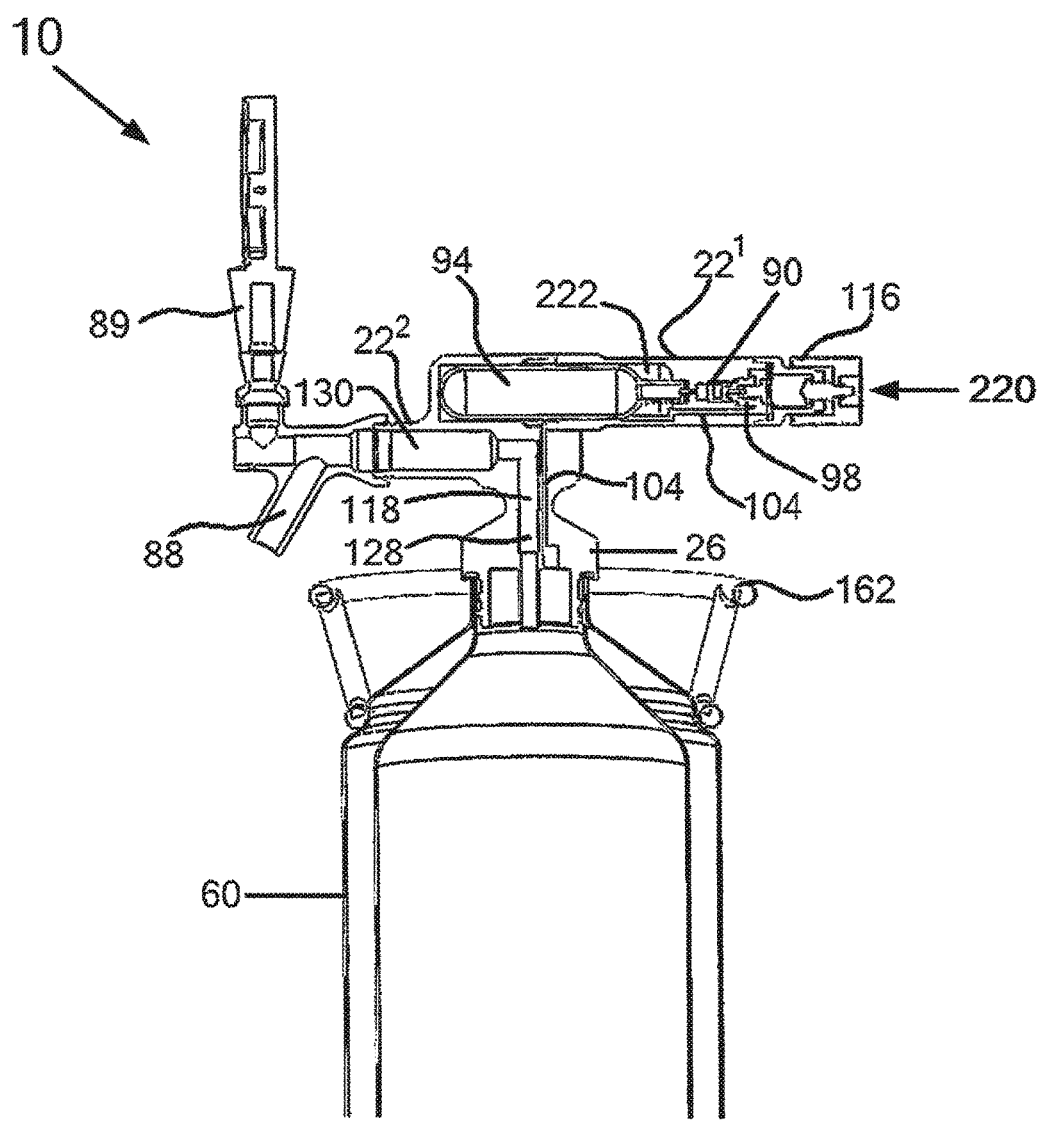
FIG. 19 includes a sectional view of the coupler half including a bi-level tap head half and vessel half, in use, according to an embodiment of the present disclosure.

As shown in FIGS. 17-19, in another embodiment the fluid pressurization and dispensing system 10 comprises a coupler 220 including a bi-level tap head $22^{bi}$ comprising a first level tap head $22^1$ and a second level tap head $22^2$, wherein the first level tap head $22^1$ is adapted for enabling for inserting the pressurized gas composition cartridge 94 within the coupler 220. This exemplary embodiment of the fluid pressurization and dispensing system 10 relates to the exemplary depicted embodiments discussed in the disclosure above, and incorporated by reference, and therefore the corresponding numbers for the features of the invention for identical elements will be the same for continuity and brevity but for the new and novel features presented.

Referring to FIG. 17-19, the coupler 220 comprises the bi-level tap head 22$^{b1}$, a shank 24, and a cap 26, contiguous thereof the coupler 220. The bi-level tap head 22$^{b1}$ defines an upper horizontal bi-cylindrical portion of the coupler 220 including the first level tap head 22$^1$ and the second level tap head 22$^2$ wherein the first level tap head 22$^1$ of the bi-level tap head 22$^{b1}$ being arranged horizontally along the x-axis 28 of the coupler 220 is oriented towards a left side of the centroidal axis 32. The first level tap head includes a first level anterior end 224 having a first level anterior opening 226 and a first level posterior end 228 having a first level posterior opening 230. The second level tap head 22$^2$ being arranged horizontally along the x-axis 28 of the coupler 20 orientated towards a right side of the centroidal axis 32 includes a second level anterior end 232 having a second level anterior opening 234 and a second level posterior end 236 having a second level posterior closed end 236, wherein the second level posterior closed end 236 of the second level tap head 22$^2$ is arranged subordinate to the first level anterior end 224 of the first level tap head 22$^1$ aligned about the centroidal axis 32.

In the depicted embodiment as shown in FIGS. 18-19 the first level tap head 22$^1$ comprises the capsule 220 integrally machined within the first level of the tap head 22$^1$ for enabling inserting the pressurized gas composition cartridge 94 within the first level of the tap head 22$^1$ such that the pressurized gas composition cartridge 94 is now in the interior of the coupler 220 and not on the exterior of the coupler 220. The gas flow channel 104 is integrally machined within the interior portion of the first level tap head 22$^1$ initiating at the gas pressure regulator 98 and terminating at the gas inlet port 112 integrally machined with the inner sole 46 of the cap 26 for enabling transmission of the flow of gas composition from the gas pressure regulator chamber 98 and into the interior 64 of the vessel 60.

The pressurized gas composition cartridge 94 is inserted within the capsule 220 and is secured by means of a closure means 240. The closure means includes a threadable closure 240 mateable with integrally machined threads within the first level anterior opening 226 of the first level of the tap head 22$^1$. The pressurized gas composition cartridge 94 is removably attached within the capsule 202 abutting the seat 100 of gas pressure regulator 90. The fistula 92 having an orifice is integrally machined operatively to the gas pressure regulator 90, wherein the fistula 92 is adapted for puncturing the closed pressurized gas composition cartridge 94 for enabling the release of the flow of gas composition through the orifice into the gas pressure regulator 90 and transmitted through the gas flow chamber 104 and purged into the interior of the vessel 60.

In this exemplary embodiment of the fluid pressurization and dispensing system 10, the gas flow channel 104 is integrally machined laterally within the first level tap head 22$^1$ having a bend at a right angle where the gas flow channel 104 extends horizontally from the gas pressure regulator chamber 90 and bends vertically towards the gas inlet port 112 adapted for enabling transmission of the flow of gas composition from the gas composition cartridge 94 through the gas pressure chamber 98 and purging of the flow of gas composition into the interior of the vessel 60 via the gas inlet port 112.

The gas flow channel 104 integrally machined within the first level of the tap head 22$^1$ of the coupler 20 provides a passage therethrough for the flow of gas composition from the pressurized gas composition cartridge 94 through a portion of the first level tap head 22$^1$ through to the gas pressure regulator 90 through a portion of the second level tap head 22$^2$, a portion of the shank 24 and through the inner sole 46 of the cap 26 to the gas inlet port 112 integrally machined within the inners sole 46 of the cap 26 which is adapted for enabling transmission of the flow of gas composition into the interior 64 of the vessel 60, wherein the gas inlet port 112 is fluidly communicable with the interior of the vessel 60 for enabling for the purging of the flow of gas composition into the vessel 60.

In this exemplary embodiment, the rotary actuator 116 releasably attached to the gas pressure regulator 90 is configured and operable to regulate the flow of gas composition between the pressurized gas composition cartridge 94 and the gas flow channel 104 thereby adjusting the volume of the flow of gas composition purged within the vessel 60 through the gas inlet port 112 disposed within the inner sole 46 of the cap 26 and into the vessel 60, as described above.

In this exemplary embodiment, as shown in FIG. 17-19 the coupler 220 includes the fluid delivery channel 118 integrally machined with the coupler 220 for enabling the delivery of the fluid 186 contained within the vessel 60 to the faucet 88. The second level tap head 22$^2$ includes the integrally machined fluid delivery outlet runner 130 and a portion of the integrally machined fluid delivery inlet runner 128 where the fluid delivery inlet runner 128 bends at a right angle toward the bore hole 62 where the fluid delivery tube 76 is operatively connected to the hose barb 82 circumventing the bore hole 62 for enabling delivery of the fluid from within the vessel 60 to the fluid delivery channel 118.

The faucet 88 is operatively connected to the second level anterior opening 234 of the second level tap head 22$^2$ and fluidly communicable with the fluid delivery outlet runner 130 for enabling a faucet operatively connected to the second level anterior opening via an attachment means, wherein the faucet 88 is adapted for receiving the fluid 186 contents from the fluid delivery channel 118 and adapted for dispensing the fluid 186 contents externally from within the vessel 60, as described above.

Referring back to FIGS. 1-8 in another embodiment of the fluid pressurization and dispensing system 10, the fluid pressurization and dispensing system 10 comprises, a coupler 20 including a rigid unitary body having an exterior surface 16 surrounding a solid interior portion 18 including a plurality of channels integrally machined within the coupler 20 wherein each of the plurality of channels is separately and rigidly autonomously supported within the interior portion 18 of the coupler 20 for enabling proper function of each of the plurality of channels, discussed in more detail below. The coupler includes an x-axis 28, a y-axis 30, and a centroidal axis 32.

As shown in FIGS. 1-4 and FIG. 8 the coupler 20 is operably connected to a vessel 60 through an attachment means for securing a vacuum seal between the coupler 20 and the vessel 60 for enabling maintaining a pressure within the vessel 60 and for dispensing of a fluid 186 contents externally from within the vessel 160.

The coupler 20, as depicted in FIGS. 6 and 7, has generally a T-shape further comprising a tap head 22 which defines an upper horizontal cylindrical portion of the coupler 20, a cap 26 which defines a lower dome portion of the coupler 20, a shank 24 which defines a vertical cylindrical waist portion of the coupler 20 is arranged being orientated vertically between the tap head 22 and the cap 26, wherein the tap head 26, the shank 24 and the cap 26 are contiguous thereof the coupler 20.

Referring to FIGS. 6-7 and FIGS. 13-14, more particularly, the cap 26 includes a crown 43 defining a top portion of the cap 26, an outer sole 44 defining a flat annular outer margin of the cap 26, a skirt 48 defining a circumferential periphery of the cap 26 between the crown 43 and the outer sole 44, an inner sole 46 defining a flat annular inner margin of the cap 26. The inner sole 46 includes a plurality of ports including a at least one gas inlet port 112 and a at least one carbonation port 114 integrally machined within the inner sole 46, a bore hole 62 circumvented by a hose barb 82 centrally disposed within the inner sole 46. Further, the cap 26 includes a plug 52 includes a plug opening 50 circumvented by a rigid cylindrical sidewall having an exterior side 56 coaxial with an interior side 58 projecting from between the outer sole 44 and the inner sole 46 of the cap 26.

Referring to FIGS. 10 and 11 the tap head 22 includes a posterior opening 40 integrally machined within a posterior end 14 of the tap head, and an anterior opening 38 integrally machined within an anterior end 12 of the tap head 22.

For implementation by the user for dispensing the fluid 186 contents from within the vessel 60 a faucet 88 is operatively connected to the anterior opening 38 of the tap head via an attachment means which is adapted for enabling receiving the fluid 186 contents contained within the vessel and adapted for dispensing the fluid 186 externally from within the vessel 186.

To enable implementation of a pressurization source, a gas injection aperture 96 is integrally machined within the tap head 22. The gas injection aperture 96 includes a fistula 92 having an orifice, the fistula 92 adapted and operable for puncturing a pre-pressurized gas composition cartridge 94 removably operatively connected thereon such that a flow of gas composition is released passing through the orifice.

To enable implementation of the regulation of the flow of gas composition, a seat 100 is integrally machined within the tap head 22 extending from the posterior opening at the posterior end of the tap head 22 wherein the seat 100 is adapted and operative for seating a gas pressure regulator 90 via an attachment means. The gas pressure regulator 100 includes a gas pressure regulator valve 211 and a gas pressure regulator chamber 98 adapted and operable for regulating the flow of gas composition from the pressurized gas composition cartridge 94 through the gas pressure chamber 98 and into the vessel 60.

The gas pressure regulator 90 is fluidly communicable to a first of the plurality of channels, a gas flow channel 104 integrally machined within the interior portion 18 of the coupler 22. The gas flow channel 104 includes an upper gas flow channel 106, and a lower gas flow channel 106 terminating at a gas inlet port 112 integrally machined within the inner sole 46 of the cap 26. The upper gas flow channel 106 is operatively fluidly communicable to the pressurized gas composition cartridge 94 for enabling transmission of the flow of gas composition from the pressurized gas composition cartridge 94 through the upper gas flow channel 106 and into the gas pressure regulator chamber 98, and the lower gas flow channel 108 is operatively fluidly communicable to the gas pressure regulator chamber 98 for enabling transmission of the flow of gas composition from the gas pressure regulator chamber 98 through the lower gas flow channel 106 through the gas inlet port 112 and into the vessel 60.

A rotary actuator 116 is operatively releasably attached to the gas pressure regulator 90 via an attachment means for enabling manual regulation by a user of the gas pressure regulator 90 for maintaining a regulated pressure within the vessel 60 and freshness of the fluid 186 contents within the vessel 60 by purging additional flow of gas composition into the vessel 60 to re-pressurize the fluid 186 contents contained in the vessel 60. The user can rotate the rotary actuator 116 to open the gas pressure chamber 98 to allow the flow of gas composition from the upper gas flow channel 106 through the gas pressure regulator chamber 98 and into the lower gas flow channel 108 for selectively dispensing a predetermined volume of gas composition pressure from the gas composition cartridge 98 into the vessel 98.

As further shown in the embodiment of FIGS. 1,3-4, 7 and 13 a gas pressure aperture 146 is integrally machined within the cap 26 adapted and operable for releasably attaching a gas pressure gauge 148 via an attachment means.

A second channel of the plurality of channels is a gas pressure channel 142 integrally machined within the cap 26 extending from the gas pressure aperture 146 to a gas pressure gauge port 146 integrally machined within the inner sole 46 of the cap 26, wherein the gas pressure channel 142 is adapted for enabling transmission of a gas pressure from within the vessel 60 through the gas pressure gauge port 146 and through the gas pressure channel 142 for measuring by the gas pressure gauge 146.

As further shown in the embodiment of FIGS. 2, 3, 4, 6 and 13 a gas pressure relief valve aperture 154 is integrally machined within the cap 26 adapted and operable for releasably attaching a gas pressure relief valve 150 via an attachment means for enabling one-directional release of a gas composition externally from within the vessel 60, wherein an activation component 158 operatively attached to the gas pressure relief valve 150 is activated upon exceeding a predetermined gas pressure level within the vessel 60.

A third channel of the plurality of channels is a gas pressure relief valve channel 146 integrally machined within the cap 26 extending from the gas pressure relief valve aperture 154 to a gas pressure relief port 156 integrally machined within the inner sole 46 of the cap 26. The gas pressure relief valve channel 146 is adapted for enabling transmission of the one-directional release of gas composition bi-products when needed externally from within the vessel 60 through the gas pressure relief port 156 through the gas pressure relief valve channel 146 and through the gas pressure relief valve 150.

In this exemplary embodiment, the gas pressure relief valve 150 can be a Belleville type spring including a Belleville spring washer held by an elastomeric hinge and operable to automatically open once a predetermined gas pressure is achieved, where a tail includes indicia indicating a volume of gas composition.

The gas pressure relief valve 150 can be configured to maintain an internal pressure within the vessel within a pre-determined range of 7 psi-60 psi. In addition, the gas pressure relief valve 150 can be configured to maintain an internal pressure within the vessel within a pre-determined range of 16 psi-60 psi.

As shown in the embodiment of FIG. 8-11 a fourth of the plurality of channels is a fluid delivery channel 118 integrally machined within the coupler 20. The fluid delivery channel 118 has a primary opening 124 and a terminal opening 130, wherein the primary opening 124 is commensurate with the bore hole 62 centrally disposed within the cap 26, and the terminal opening 130 commensurate with the anterior opening 38 of the tap head 22. The fluid delivery channel 118 includes a fluid delivery inlet runner 128 fluidly communicable to a fluid delivery outlet runner 130 adapted and operable for directing transmission of the fluid 186 contained within the vessel 60 upstream to the faucet 88 when the faucet 88 is dispensed by the user.

The primary opening 124 of the fluid delivery channel receives a fluid delivery tube 76. The fluid delivery tube 76 has a first end 78 having a first opening operatively connected to the hose barb 82 circumventing the bore hole 62 and a second end 80 having a second opening provided immersed within the fluid 186 contained within the vessel 60 for enabling delivery of the fluid 186 contained within the vessel 60 therethrough to the fluid delivery channel 118.

In the exemplary embodiment, the cap 26 further comprising a plurality of perforations 138, as depicted in FIG. 15 integrally machined within the inner sole 46 of the cap 26, wherein each of the plurality of perforations 138 includes a pore 134 opening fluidly communicative with the interior 64 of the vessel 60 adapted and operable for enabling an increased transmission of the flow of gas composition from the lower gas flow channel 108 into the interior of the vessel by means of simultaneous purging of the flow of gas composition through the plurality of perforations 138 into the vessel 60.

In this exemplary embodiment, as depicted in FIGS. 9-11 and 14 the cap 26 includes a carbonation port 114 integrally machined within the inner sole 46 of the cap 26, the carbonation port 114 is operatively communicable with the pressurized gas composition cartridge 94 and the interior 64 of the vessel 60, wherein the carbonation port 114 is operatively connected to a carbonation tube (not shown) for enabling carbonation of a liquid contained in the vessel 60.

Referring back to FIGS. 1-3, 6 and 16 the vessel 60 is a vessel 60 cable of containing a fluid under pressure. The vessel 60 includes a single unitary body including a bottom 75 and peripheral double-side walls 160 surrounding an interior 64 having a cavity operable to contain a fluid 186 therein under pressure, a neck 68 defining upstanding side walls 71 proud of a shoulder portion 65 of the vessel 60 including a neck opening 72 defined by a circumferential rim 74 wherein the neck 68 includes a neck finish 70 which is mateable with the plug finish 53 of the coupler 20 adapted for enabling releasably attaching the vessel 60 to the coupler 20.

In an embodiment of the present disclosure the attachment means for releasably attaching the coupler 20 to the vessel 60 comprises a threaded plug finish 53, wherein the threaded plug finish 53 comprises one or more of the following: a 1 thread turn, a 1.5 thread turn, a 2 thread turn having a tail dimension, a 2 thread turns with narrow threads, a 2 thread turns with buttress finish and thick threads, a 1 thread turn with non-continuous thread having a lug finish, and a 1 thread turn having a tail dimension.

The fluid can be a liquid, gas, a carbonated liquid beverage, or a non-carbonated liquid beverage, beer, wine, soda, seltzer, water being vacuum sealed under pressure. The vessel 60 includes an interior cavity 64 including a peripheral side walls 66 configured and operable to maintain a volume of fluid under pressure therein. The peripheral side walls 66 converge to a limited degree forming a shoulder 65 of the vessel 60. The peripheral side wall 66 comprise double-walled side walls 160.

The vessel 62 is configured having double-walled side walls 160 because the double-walled side walls 160 provide an interior chamber 64 operable to provide temperature insulation for fluids 186, more particularly liquids, particularly liquid beverages for consumption, held in the vessel 62. The vessel 60 includes a flat peripheral exterior base 75 having a concave center 79 so that the vessel 60 can be positioned upon a flat surface without tipping. The concave center 79 of the vessel 60 is configured in the interior of the vessel 60. The concave center 79 configuration is beneficial when a small amount of volume of liquid remains in the vessel 60. The fluid delivery tube 76 can reach the remaining small volume of liquid beverage 186 from around the periphery of the bottom of the vessel 60 such that the user can enjoy the last drop of liquid beverage 186.

As shown in FIGS. 8 and 16, a neck 68 of the vessel 60 is formed from upstanding peripheral sidewalls 71 extending proud of the shoulder 66 of the vessel 60. The neck 68 terminates at a neck opening 72 which is circular, wherein the neck opening 72 is fluidly communicable to the plurality of ports including the at least one gas inlet port 112 integrally machined within the inner sole 46 of the cap 26 when the coupler 20 is releasably attached to the vessel 60 under the vacuum seal.

The neck 68 includes a neck finish 76 having the upstanding peripheral sidewalls 63 terminating in a neck opening 72 defined by a circumferential rim 74. The neck finish 76 is configured and operable for releasably attaching to a plug 52 of the coupler 20, the plug 52, having a mateable plug finish 53 to the neck finish 76, described in more detail below.

Referring to FIGS. 1-3 and FIG. 8, the vessel 60 further includes a chime 162 permanently mounted to a portion of the shoulder 66 of the vessel 60. The chime 62 includes a bottom handle ring 164 having a circumference ($C^1$) and a top handle ring 166 having a circumference ($C^2$) which is greater than the circumference $C^1$ of the bottom handle ring 164. The bottom handle ring 164 is joined by a plurality of outwardly extending rigid spokes 168 to the top handle ring 166, such that each outwardly extending rigid spoke 168 has an equal length ($L^4$) and are equally spaced separate and apart from each other rigid spoke 168 at a width ($W^1$) measured along the bottom handle ring 164 and, accordingly, the rigid spokes 168 are equally spaced separate and apart from each other at a width ($W^2$) measured along the top handle ring 166 such that a plurality of handle spaces 170 are formed each having generally a trapezoid shape each including a base $b_1$, and a base $b_2$, and a height h adapted to facilitate hand holds 171. The handle spaces 170 each topped at the hand holds 171 are configured to allow a user's hands to be presented therethrough so that the user can grab the hand holds 171 allowing the user to easily carry and transport the vessel 62.

The chime 162 is manufactured from a food-grade material, for example, stainless steel. in an embodiment of the present invention it is preferred that the chime is manufactured from stainless steel which is rigid and has sufficient mass to allow for manipulation of the vessel 62, particularly, when the vessel 62 contains a full volume of fluid 186. The chime 162 is permanently mounted to the vessel 62 by means of welding to minimize the chime 162 from becoming loose when manipulating the vessel 62.

In an embodiment of the present disclosure, the top handle ring 166 further includes at least one curve (not shown) along an edge of the top handle ring 166 to conform in shape to a liquid receptacle, for example, glassware, to be supported in contacting relation therealong when the liquid 186 is dispensed from the faucet 88 into the liquid receptacle, or glassware. For a beneficial dispensing of the liquid 186 from the faucet 88, the chime 166 is configured a distance from the coupler 20 so that the glassware can be held at a 45 degree angle, as shown in FIG. 1, showing the glassware positioned upon the top handle ring 166 of the chime 162 and the liquid 186 is dispensed into the glassware from the faucet 88.

Referring more closely to FIGS. 6-7 and 9-12 the coupler 20 comprises a single body unit comprising a tap head 22, a shank 24, and a cap 26, having a plug 52. By this arrangement, the entire coupler 20 is unitary and each of the tap head 22, the shank 24, the cap 26 and the plug 52 are contiguous of the rigid single body unit and accordingly there is no need for additional connections between the exterior surface 16 to maintain the contiguous parts therein the single body unit of the coupler 20. The vessel 60 capable of being vacuum sealed is configured to contain a volume of fluid 186 under pressure.

With reference to FIGS. 1-3 and FIGS. 6-9, and FIGS. 18-20 in the exemplary embodiments disclosed of the present invention the fluid pressurization and dispensing system includes the coupler 20 realeasably attached to the vessel 60 via an attachment means. In the exemplary embodiments the attachment means is a plug opening having integrally machined threads within the plug finish and a threaded neck opening having mateably threads integrally machined within the neck finish according to the embodiments of FIGS. 6-8 and 16. The attachment means enables for securely releasably attaching the coupler 20 to the vessel 60 to maintain the vacuum seal.

In the exemplary embodiment of the fluid pressurization and dispensing system the attachment means for releasably attaching the coupler 20 to the vessel 60 for securing a vacuum seal between the coupler and the vessel and for maintaining a regulated pressure of a fluid contained within the vessel comprises a threaded plug finish 53 and a mateable threaded neck finish 70 as shown in FIGS. 6-8 and 16, respectively. As shown in FIGS. 6 and 7 the coupler 20 includes a plug 52 having a plug finish 53 with integrally machined exterior threads, wherein the plug finish 53 is adapted for enabling releasably attaching the vessel 60 including a neck 68 having a neck finish 70 with integrally machined interior threads.

The threaded plug opening 55 in the exemplary embodiment of the present invention, can include the threaded plug finish 53 one or more of the following: a 1 thread turn, a 1.5 thread turn, a 2 thread turn having a tail dimension, a 2 thread turns with narrow threads, a 2 thread turns with buttress finish and thick threads, a 1 thread turn with non-continuous thread having a lug finish, a 1 thread turn having a tail dimension, each of which of the plug finishes 53 is mateable to the neck finish 70 of the vessel 60 for enabling for releasably attaching the coupler 20 to the vessel 60 for maintaining a leak proof vacuum seal.

In an exemplary embodiment of the present invention, the plug 52 includes a plug finish 53 having a 2-thread turn for enabling the coupler to be releasably attachable to a variety of types of vessels 60.

In another embodiment of the present disclosure, the coupler 20 includes plug finish 53 having integrally machined interior threads which are mateable with integrally machined exterior threads of the neck finish 73 of the neck 68 for enabling releasably attaching the coupler 20 to the vessel 60.

In another embodiment of the present disclosure the attachment means for releasably attaching the coupler 20 to the vessel 60 for securing a vacuum seal between the coupler 20 and the vessel 60 and for maintaining a regulated pressure of a fluid contained within the vessel comprises one or more of the following: a ferromagnetic plug finish with mateable ferromagnetic neck finish, a snap fit plug finish 70 with mateable snap fit neck finish, an insertable opening plug finish with a mateable receiving neck finish 70, a ferromagnetic cap which is plug-less with mateable ferromagnetic neck circumferential rim.

In another embodiment of the present disclosure, the attachment means for releasably attaching the coupler 20 to the vessel 60 can comprise one or more of the following: a threaded opening, a ferromagnetic opening, a snap fit opening, and insertable opening.

In another embodiment of the present disclosure, the inner sole 46 of the cap 26 of the coupler 26 is integrally machined with a ferromagnetic material and the circumferential rim 74 of the neck 68 of the vessel 60 is integrally machined with a mateable ferromagnetic material adapted and operable for enabling the coupler 20 for releasably attaching to the vessel 60 and maintaining a vacuum seal between the coupler 20 and the vessel 60.

In another embodiment of the present invention, the plug 52 does not include a plug finish 29 having threads, and the neck 68 of the vessel 60 does not include a neck finish 76 having threads.

In another embodiment of the fluid pressurization and dispensing system, the coupler includes an adaptor (not shown). The adaptor includes a unitary attachment member, wherein the adaptor includes attachment means having a first attachment end having a first attachment opening and a second attachment end having a second attachment opening, wherein the first attachment opening is adapted for operatively connecting to the coupler 20 and the second attachment opening is adapted for operatively connecting to any one of a standard commercially available vessel 60 for containing a fluid 186 under pressure.

The vacuum seal between the neck 68 of the vessel 60 and the coupler 10 can be maintained by use of an adaptor 178 (not shown) comprising a ferromagnetic element. In an embodiment of the present disclosure, the ferromagnetic element is a magnet.

In another embodiment of the present disclosure, the adaptor includes an attachment means for releasably attaching the coupler 20 to the vessel 60 can comprise one or more of the following: a threaded opening, a ferromagnetic opening, a snap fit opening, and insertable opening.

As way of example, in the embodiment of the fluid pressurization and dispensing system 10 with reference to FIGS. 1-19 the fluid 186 can be a liquid beverage for consumption by the user, for example, a carbonated liquid, more particularly, beer, or a nitro-beer, which can generally be filled, for example, directly from a commercial beer tap. As the beer exits the commercial beer tap, the beer will generally have sufficient carbonation to initially maintain the initial $CO_2$ level and, therefore, issue an adequate initial carbonation of the beer evidenced by its flavor and taste to the consumer. The liquid beverage is filled into the vessel 60 providing an initial head space 67 of below the neck of the vessel 60. Once the vessel 60 is filled, the vessel 60 is tightly closed creating a vacuum seal by means of releasably threadably attaching the coupler 20 via the plug 52 to the neck 68 of the vessel 60.

Figure 2:
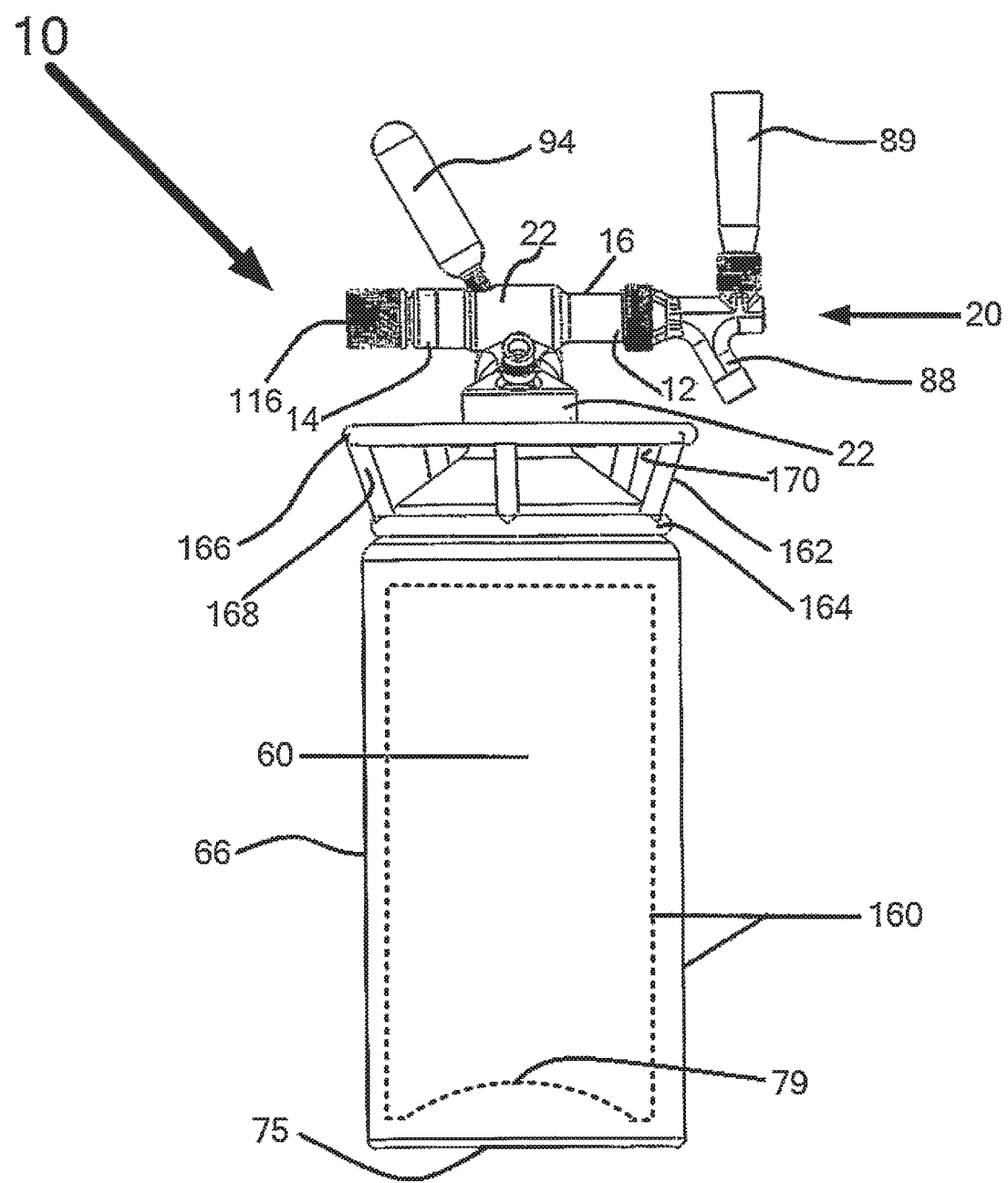
FIG. 2 illustrates an isometric view of a rear perspective view of the fluid pressurization and dispensing system showing a coupler and a vessel in use of FIG. 1.
Figure 3:
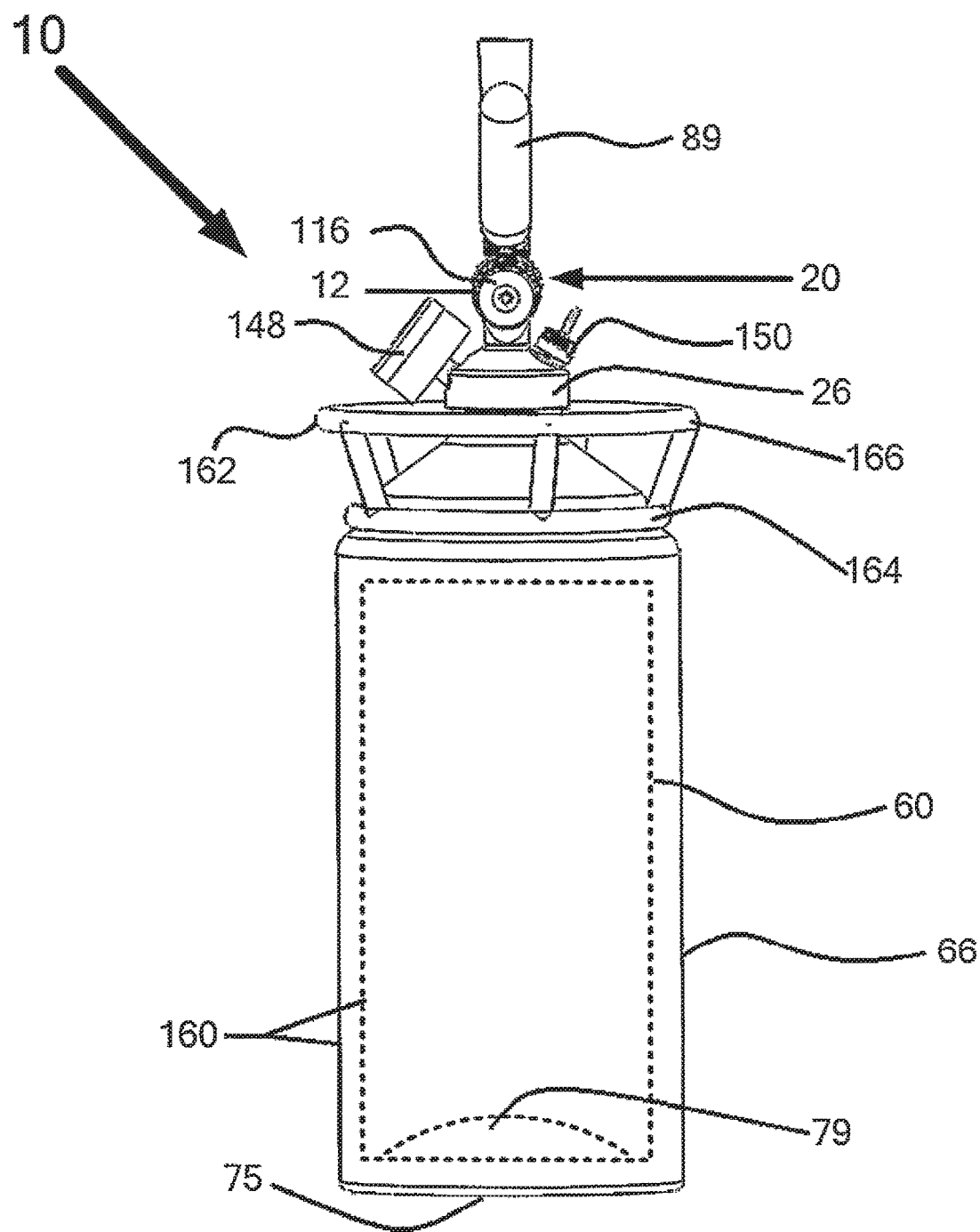
FIG. 3 illustrates a side elevation view of the fluid pressurization and dispensing system showing a coupler and a vessel in use of FIG. 1, according to an embodiment of the present disclosure.
Figure 4:
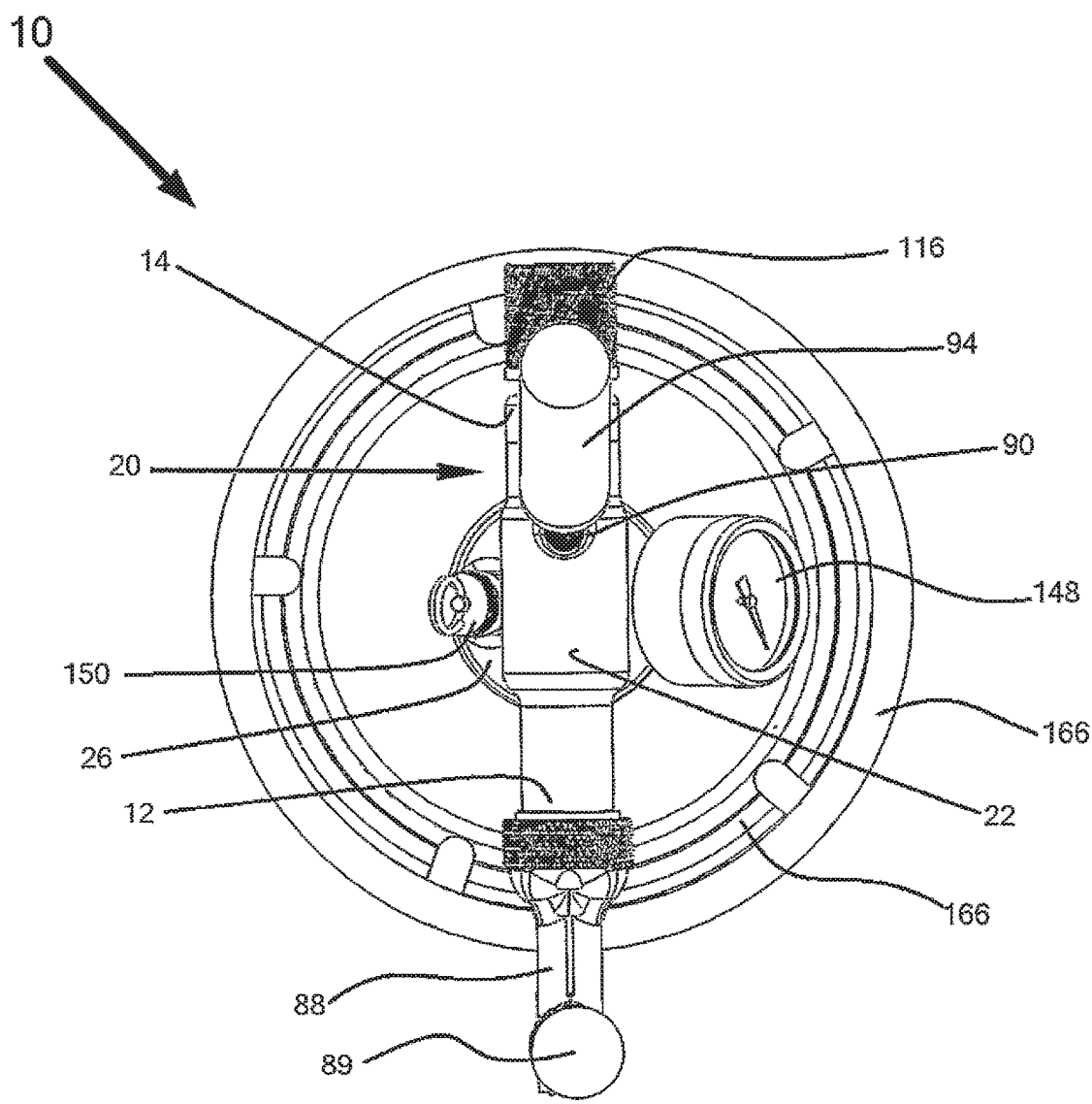
FIG. 4 illustrates a top plan view of the fluid pressurization and dispensing system of FIG. 1, according to an embodiment of the present disclosure.
Figure 5:
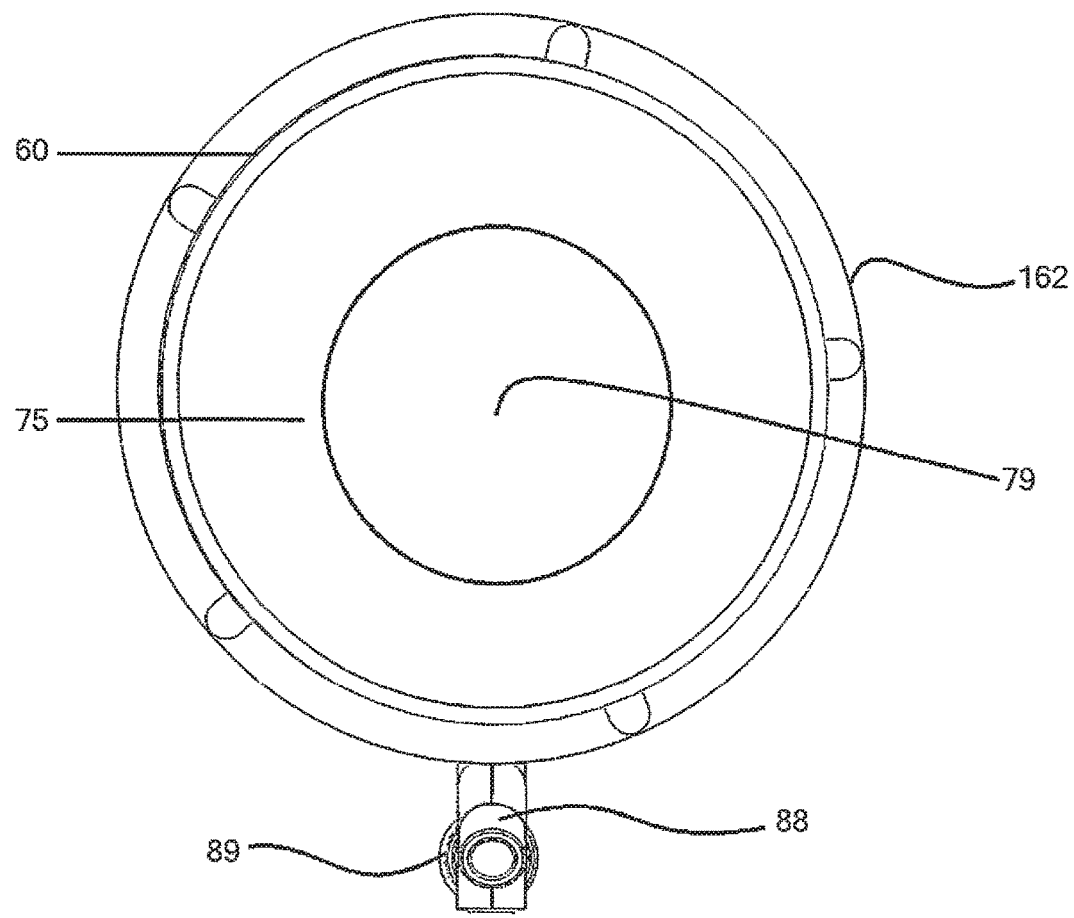
FIG. 5 illustrates a bottom plan view of the fluid dispensing system of FIG. 1, according to one embodiment of the present disclosure.

In a preferred embodiment of this exemplary disclosure, as shown in FIGS. 1-3 the vessel 60 includes the peripheral side walls 66 that are double-walled side walls 160. The double walled side walls 160 of the vessel 60 are made of stainless steel. The double walled side walls 160 of the vessel 62 can be made of any material that is food-grade material but in an embodiment of the present invention, the vessel 60 is preferred to be made of stainless steel. In another embodiment of the present invention, the double walled side walls 160 are made of aluminum. In another embodiment the vessel 60 is made with a peripheral side wall 66 having a single wall.

In the preferred embodiment of the present disclosure, the coupler 20 is manufactured with food-grade stainless steel. In an embodiment of the present invention the vessel 60 is a 1 gallon capacity vessel capable of being pre-pressurized and that can be vacuum sealed under pressure. In another embodiment of the present invention the vessel 60 is a 2 gallon capacity vessel capable of being pre-pressurized and that can be vacuum sealed under pressure.

As will be understood and appreciated, however, many other vessels that are used for pressurization and preservation of fluids may be used in conjunction with the coupler 20 as described in the present disclosure. In another embodiment of the present invention, the fluid pressurization and dispensing system 10 can include a keg, a wine vessel, a soda vessel or any vessel capable of being pre-pressurized and adapted to contain a fluid therein. The fluid can be a liquid beverage. In another embodiment, the liquid is a liquid beverage able to be carbonated under pressure. In another embodiment the liquid is a non-carbonated liquid. The liquid beverage can be beer, wine, soda, seltzer, water, juice, or any consumable liquid beverage.

In another embodiment of the present invention, the fluid can be a gas. The gas can be argon gas.

In an exemplary embodiment of the present invention, the fluid pressurization and dispensing system 10 can be used implementing the liquid beverage known as "nitro" beers.

Nitrogen dispensed beer, or "nitro" primarily utilizes $N_2$ and $CO_2$ in its carbonation. The "nitro" beer is dispensed, in this exemplary embodiment using the coupler 20 and a removable restrictor plate (not shown) positioned on the nozzle such that the nozzle is abutting a nitro-faucet (not shown), wherein the nitro-faucet is releasably attached to the nozzle 84. The nitro-beer faucet uses a diaphragm, the restrictor plate and a flow straightener to cream the beer. The nitro-faucet includes a spring loaded cam-actuator plunger style valve.

The faucet comprises a faucet selected from the group comprising of, a standard, a ventless with shaft, a ventless without shaft, a nitro-faucet, a spring loaded cam-actuated, and a roto-faucet. The faucet 88 can include a faucet adaptor adapted for releasably attaching a European beer faucet. The faucet 88 can, also, include a faucet adaptor adapted for releasably attaching a flow control faucet. When dispensing nitro-beer, the faucet is a stout faucet comprising a removable restrictor plate and operable to regulate the flow of a fluid through the faucet.

In the exemplary embodiment, the pressurized gas composition cartridge 94 comprises one or more of the following: a disposable pre-pressurized $N_2$ and $CO_2$ gas composition cartridge, a disposable pre-pressurized $N_2$ gas composition cartridge, a disposable pre-pressurized $CO_2$ gas composition cartridge, a disposable pre-pressurized argon cartridge. In addition, the pressurized gas composition cartridge comprises one or more of the following: a refillable pre-pressurized $N_2$ and $CO_2$ gas composition cartridge, a refillable pre-pressurized $N_2$ gas composition cartridge, a refillable pre-pressurized $CO_2$ gas composition cartridge, a refillable pre-pressurized argon gas composition cartridge.

The fluid pressurization and dispensing system 10, includes an adaptor 178 adapted for releasably attaching the coupler 20 to any standard commercially available vessel 60 that can contain a fluid under pressure and maintain a vacuum seal. The adaptor adapted for releasably attaching the coupler 20 to the vessel 60, the adaptor 178 (not shown) including two opposing attachment ends, a first attachment end having a first attachment opening, and a second attachment end having a second attachment opening, wherein the first attachment opening includes a first attachment means adapted and operable for releasably attaching to the plug opening 50 of the coupler 20, and the second attachment opening includes a second attachment means adapted and operable for releasbly attaching to the neck opening 72 of the vessel 60.

In another embodiment of the fluid pressurization and dispensing system the adaptor 178 (not shown) includes a unitary attachment member, the adaptor 178 including an attachment means having a first attachment end having a first attachment opening and a second attachment end having a second attachment opening, wherein the first attachment opening is adapted for operatively connecting to the coupler 20 and the second attachment opening is adapted for operatively connecting to a standard commercially available vessel 60 for containing a fluid under pressure.

In an exemplary embodiment, the fluid pressurization and dispensing system the plug 52 of the coupler 20 includes exterior threads integrally machined on the exterior side 56 of the plug finish 53 and the neck 68 of the vessel 60 includes interior threads mateable with the exterior threads of the plug finish 53 for enabling releasably attaching the coupler 20 to the vessel 60.

In another exemplary embodiment of the present invention, the plug 52 includes interior threads integrally machined on the interior side 58 of the plug finish 53 and the neck 68 of the vessel 60 includes exterior threads mateable with the interior threads of the plug finish 53 for enabling releasably attaching the coupler 20 to the vessel 60.

In another embodiment of the present invention, the plug 52 of the coupler 20 includes a non-threaded plug finish 53 mateable with a non-threaded neck finish 70 of the neck 68 of the vessel 60 for enabling releasably attaching the coupler 20 to the vessel 60.

In another embodiment of the present disclosure, the inner sole 46 of the cap 26 is integrally machined with a ferromagnetic material and the circumferential rim 74 of the neck 68 of the vessel 60 is integrally machined with a mateable ferromagnetic material for enabling the coupler 20 to be releasably attach to the vessel 60 and operable for maintaining a vaccum seal between the coupler 20 and the vessel 60.

In an embodiment of the present disclosure, the pressurization and liquid dispensing system 10 is provided in a kit 184 (not shown). The kit 184 comprising, at least one of the fluid pressurization and dispensing systems 10, as described in detail above according to the embodiment of FIGS. 1-16, and a at least one of the fluid pressurization and dispensing systems 10, as described in detail according to the embodiment of FIGS. 17-19, wherein the coupler 20 comprises a bi-level tap head, as described above depicted in FIGS. 17-19, wherein the kit comprises a at least one coupler 20; a at least one vessel 60; a at least one liquid delivery tube 76; a at least one pressurized gas composition cartridge 94; a at least one faucet 88; a at least one pre-pressurized gas pressure gauge 148; a at least one gas pressure relief valve 150; a at least one removable restrictor plate 172; a at least one label including indicia identifying the fluid 186 contained within the vessel 60; and a at least one adaptor; a at least one instructions of use including instruction sheets for enabling assembly of elements of the fluid pressurization and dispensing system kit 184, the elements comprising, the at least one coupler 20, the at least one vessel 60, the at least one fluid delivery tube 76, the at least one faucet 88, the at least one pre-pressurized gas composition cartridge 94, the at least one gas pressure relief valve 150, the at least one gas pressure gauge 148, the at least one restrictor plate 172, the at least one label, and the at least one adaptor.

The kit 184 can, also, include the bi-level tap head 22$^{b1}$, as described above according to the embodiment of FIGS. 17-19.

In another embodiment the liquid dispensing system can be provided in a kit 186 (not shown) including a plurality of components. The kit 186 comprising, a plurality of a plurality of fluid pressurization and dispensing systems 10 comprising, a plurality of couplers 20; a plurality of vessels 60; a plurality of fluid delivery tubes 76; a plurality of a pre-pressurized gas cartridges 94; a plurality of faucets 88; a plurality of fluid delivery tubes 76; a plurality of removable restrictors a plurality of adaptors 178.

The features of the coupler 20 described above can be used with a variety of vessels 60 manufactured with food-grade materials, including single walled vessels manufactured with glass, cement, rigid polyvinyl, and silicone dimensioned for smaller vessels and larger vessels.

This disclosure is primarily focused on a portable system which is suitable for any institution or household for the purpose of dispensing of a variety of liquid beverages, such as, but not limited to beer, wine, soda, carbonated water, and the storage of such beverages in such a system when the beverage has not been subject to traditional packaging methods, such as bottling, canning, kegging, but in the alternative is obtained in a "draft" form. The beer is from a tap such as, but not limited to, in a micro-brewery, a bar, sports bar, restaurant, liquor merchant, tap room, brewery, and the like, or provided directly from a fermentation vessel, such as, but not limited to, a fermentation tank or bright tank.

While the present disclosure is focused on beer, and wine dispensing, and carbonation of a liquid beverage, it should be recognized that the fluid pressurization and dispensing system, the methods of use, the kit, can be used for any carbonated fluid. This can include, but is not limited to, sodas, carbonated fruit juices, cider, peary, mead, energy drinks, wines, sparkling wines, carbonated waters, and any combinations thereof. In addition, while the system, methods, and kit are particularly useful for carbonated liquid beverages the system can, also, be used to dispense non-carbonated beverages as well, such as, but not limited to, wine, liquors, waters, fruit drinks, milk, soy milk, almond milk, chocolate milk, coffee, tea, and non-carbonated soft drinks.

The foregoing description of the exemplary embodiments have been presented only for purposes of illustration and description and is not intended to be exhaustive or to limit aspects of the present disclosure to the precise forms disclosed for allowing the coupler to seal a vessel under pressure and enable maintaining pre-pressurization of the vessel, pressurization, and re-pressurizing of the fluid contents within the vessel and dispensing of the fluid contents externally from within the vessel.

In view of the many possible embodiments to which the principles of the disclosed invention may be applied, it should be recognized that the illustrated embodiments are only preferred examples of the invention and should not be taken as limiting the scope of the invention. It will be evident that various modifications may be made thereto without departing from the broader spirit and scope of the invention as set forth. The specification and drawings are, accordingly, to be regarded in an illustrative sense rather than a restrictive sense.

We claim:

1. A fluid pressurization and dispensing system, comprising:

a coupler having a rigid single body unit having generally a "T" shape, wherein the coupler includes a tap head, a shank, and a cap which are contiguous thereof the coupler, the coupler having an exterior surface which surrounds an interior portion which is solid, wherein the interior portion includes a plurality of channels each integrally machined within the interior portion each having a hollow tubular configuration extending therethrough the interior portion to a portion of the exterior surface, the coupler adapted and operable for releasably attaching to a vessel through an attachment means for enabling securing a vacuum seal between the coupler and the vessel for maintaining pressure within a vessel and dispensing of a fluid contents externally from within the vessel;

a mass with a surface density;

a y-axis, an x-axis, a centroidal axis;

the tap head defines an upper horizontal cylindrical portion of the coupler, the tap head including an anterior end and a posterior end having a length $L^1$ extending laterally along the x-axis therebetween, a ventral side and a dorsal side having a cross-diameter ($CD^1$), the anterior end having an anterior opening and the posterior end having a posterior opening;

the shank defines a vertical cylindrical waist portion of the coupler, the shank including a proximal end and a distal end having a length $L^2$ therebetween and a cross-diameter ($CD^2$), the proximal end extending axially towards the ventral side of the tap head and the distal end extending axially towards the cap along the centroidal-axis;

the cap defines a lower dome portion of the coupler, the cap including a crown defining a top portion of the cap, an outer sole defining a flat annular outer margin of the cap, a skirt defining a circumferential periphery of the cap between the crown and the outer sole, an inner sole defining a flat annular inner margin of the cap, wherein the inner sole includes a plurality of ports including at least one gas inlet port integrally machined therein, a bore hole circumvented by a hose barb centrally disposed within the inner sole, a plug includes a plug opening circumvented by a rigid cylindrical sidewall having a plug finish having an exterior side coaxial with an interior side projecting a length $L^3$ from between the outer sole and the inner sole of the cap and having a cross-diameter ($CD^3$);

a gas injection aperture having threads integrally machined within the dorsal side of the tap head, wherein the gas injection aperture includes a fistula having an orifice, the fistula adapted and operable for puncturing a pressurized gas composition cartridge releasably threadably attached thereon such that a flow of gas composition is released passing through the orifice;

a seat integrally machined within the tap head extending from the posterior opening, the seat adapted and operative for releasably attaching a gas pressure regulator via an attachment means, the gas pressure regulator including a gas pressure regulator valve and a gas pressure regulator chamber and operable for regulating the flow of gas composition;

a first channel of the plurality of channels is a gas flow channel integrally machined within the interior portion of the coupler, the gas flow channel includes an upper gas flow channel having a first bend, and a lower gas flow channel having a second bend, wherein the upper gas flow channel is operatively fluidly communicable to the orifice of the gas injection aperture for enabling transmission of the flow of gas composition from the pressurized gas composition cartridge through the upper gas flow channel and into the gas pressure regulator chamber, and the lower gas flow channel is operatively fluidly communicable to the gas pressure regulator chamber for enabling transmission of the flow of gas composition from the gas pressure regulator chamber through the lower gas flow channel through the gas inlet port and into the vessel;

a rotary actuator operatively releasably attached to the gas pressure regulator via an attachment means for enabling regulation of the flow of gas composition from the upper gas flow channel through the gas pressure regulator chamber and into the lower gas flow channel for selectively dispensing a predetermined volume of gas composition pressure into the vessel for maintaining a regulated pressure within the vessel;

a gas pressure aperture having threads integrally machined within a forward portion of the cap adapted and operable for releasably threadably attaching a gas pressure gauge via an attachment means;

a second channel of the plurality of channels is a gas pressure channel integrally machined within the cap extending from a caudal end of the gas pressure aperture to a gas pressure gauge port integrally machined within the inner sole of the cap, wherein the gas pressure channel is adapted for enabling transmission of a gas pressure from within the vessel through the gas pressure gauge port and through the gas pressure channel for measuring by the gas pressure gauge;

a gas pressure relief valve aperture having threads integrally machined within a rearward portion of the cap adapted and operable for releasably attaching a gas pressure relief valve via an attachment means for enabling one-directional release of a gas composition externally from within the vessel, wherein an activation component operatively attached to the gas pressure relief valve is activated upon exceeding a predetermined gas pressure level within the vessel;

a third channel of the plurality of channels is a gas pressure relief valve channel integrally machined within the cap extending from a base end of the gas pressure relief valve aperture to a gas pressure relief port integrally machined within the inner sole of the cap, wherein the gas pressure relief valve channel is adapted for enabling transmission of the one-directional release of gas composition externally from within the vessel through the gas pressure relief port through the gas pressure relief valve channel and through the gas pressure relief valve;

a fourth channel of the plurality of channels is a fluid delivery channel integrally machined within the coupler having a right angle bend, the fluid delivery channel having a primary opening and a terminal opening, the primary opening commensurate with the bore hole centrally disposed within the cap, and the terminal opening commensurate with the anterior opening of the tap head, the fluid delivery channel includes a fluid delivery inlet runner fluidly communicable to a fluid delivery outlet runner adapted and operable for the transmission of a flow of the fluid from within the vessel and upstream to a nozzle;

a fluid delivery tube adapted for enabling transmission of the fluid contained from within the vessel to the fluid delivery channel, wherein the fluid delivery tube includes a first end and a second end having a length $L^4$ therebetween and a cross-diameter ($CD^4$), wherein the first end having a first opening is operatively connected to the hose barb, and the second end having a second opening is provided immersed therein the fluid contained within the vessel;

a carbonation port integrally machined within the inner sole of the cap;

a faucet operatively connected to the nozzle via an attachment means, wherein the faucet is adapted for receiving the fluid contents from the fluid delivery channel and adapted for dispensing the fluid contents externally from within the vessel; and the vessel includes a single unitary body including a bottom and peripheral double-side walls surrounding an interior having a cavity operable to contain a fluid therein under pressure, a neck defining upstanding side walls extending upward from a shoulder portion of the vessel having a length L 5 including a neck opening defined by a circumferential rim having a cross-diameter ($CD^5$), wherein the neck includes a neck finish which is mateable with the plug finish of the coupler adapted for enabling releasably attaching the vessel to the coupler.

2. The fluid pressurization and dispensing system of claim 1, further comprising a plurality of perforations integrally machined within the inner sole of the cap, wherein each of the plurality of perforations includes a pore opening fluidly communicative with the interior of the vessel adapted and operable for enabling an increased transmission of the flow of gas composition from the lower gas flow channel into the interior of the vessel by means of simultaneous purging of the flow of gas composition through the plurality of perforations into the vessel.

3. The fluid pressurization and dispensing system of claim 1, wherein the carbonation port is operatively fluidly communicable with the gas flow channel for enabling transmission of a flow of gas from the pressurized gas composition cartridge into the vessel for carbonation of a non-carbonated fluid contained within the vessel, wherein a carbonation tube is operatively connected to the carbonation port for enabling transmission of the flow of pressurized gas composition into the vessel.

4. The fluid pressurization and dispensing system of claim 1, wherein the attachment means for releasably attaching the coupler to the vessel comprises one or more of the following: a threaded plug finish mateable with a threaded neck finish, a ferromagnetic plug finish mateable with a ferromagnetic neck finish, and a snap fit plug finish mateable with a snap fit neck finish.

5. The fluid pressurization and dispensing system of claim 4, wherein the ferromagnetic plug finish is a magnet.

6. The fluid pressurization and dispensing system of claim 1, wherein the attachment means for releasably attaching the coupler to the vessel comprises a threaded plug finish, wherein the threaded plug finish comprises one or more of the following: a 1 thread turn, a 1.5 thread turn, a 2 thread turn having a tail dimension, a 2 thread turns with narrow threads, a 2 thread turns with buttress finish and thick threads, a 1 thread turn with non-continuous thread having a lug finish, and a 1 thread turn having a tail dimension.

7. The fluid pressurization and dispensing system of claim 1, wherein the attachment means for releasably attaching the coupler to the vessel for securing a vacuum seal between the coupler and the vessel is one or more of the following: a threaded opening, a ferromagnetic opening, a snap fit opening, and an insertable opening.

8. The fluid pressurization and dispensing system of claim 1, further comprising an adaptor including a unitary attachment member, wherein the adaptor includes attachment means having a first attachment end having a first attachment opening and a second attachment end having a second attachment opening, wherein the first attachment opening is adapted for operatively connecting to the coupler and the second attachment opening is adapted for operatively connecting to any one of a standard commercially available vessel for containing a fluid under pressure.

9. The fluid pressurization and dispensing system of claim 8, wherein the adaptor includes an attachment means for releasably attaching the coupler to the vessel comprises one or more of the following: a threaded opening, a ferromagnetic opening, a snap fit opening, and insertable opening.

10. The fluid pressurization and dispensing system of claim 1, wherein the inner sole of the cap of the coupler is integrally machined with a ferromagnetic material and the circumferential rim of the neck of the vessel is integrally machined with a mateable ferromagnetic material adapted and operable for enabling the coupler for releasably attaching to the vessel and maintaining a vacuum seal between the coupler and the vessel.

11. The fluid pressurization and dispensing system of claim 1, wherein the upper gas flow channel is v-shape and passes through the tap head of the coupler, and lower gas flow channel is an inverted L-shape and passes through the tap head, the shank, and the cap of the coupler.

12. The fluid pressurization and dispensing system of claim 1, wherein the fluid delivery channel is an inverted L-shape, wherein the fluid delivery inlet runner defines a vertical portion of the inverted L-shape passing from the bore hole therethrough a centroidal portion of the cap, the shank, and the tap head, and the fluid delivery outlet runner defines a horizontal portion of the inverted L-shape passing through a central portion of the tap head along the x-axis and terminating at a nozzle opening.

13. The fluid pressurization and dispensing system of claim 1, wherein the fluid delivery outlet runner is a converging-diverging channel, the converging-diverging channel adapted and operable for regulating the transmission of the flow of the fluid during dispensing of the fluid externally from within the vessel.

14. The fluid pressurization and dispensing system of claim 1, wherein the fluid delivery outlet runner is a horizontal venturi flow meter adapted and operable for regulating the transmission of the fluid externally from within the vessel.

15. The fluid pressurization and dispensing system of claim 1, wherein the fluid delivery outlet runner is tapered configured and operable for regulating the transmission of the fluid externally from within the vessel.

16. The fluid pressurization and dispensing system of claim 1, wherein the gas pressure regulator further comprises a first o-ring provided at the base end of a disc of the gas pressure regulator, a second o-ring provided at a lip of the disc, and a non-porous membrane disposed transversely between a bonnet of the gas pressure regulator and the disc, are adapted and operable for providing a leak-proof barrier to the gas pressure chamber for sealing against any backflow of the gas composition.

17. The fluid pressurization and dispensing system of claim 16, wherein the non-porous membrane is manufactured with nitrile rubber.

18. The fluid pressurization and dispensing system of claim 1, wherein the coupler comprises at least two gas injection apertures integrally machined within the tap head adapted and operable for simultaneously releasably attaching of two individual pressurized gas composition cartridges to the coupler.

19. The fluid pressurization and dispensing system of claim 1, wherein the pressurized gas composition cartridge comprises a pre-pressurized CO2 gas composition cartridge that is refillable.

20. The fluid pressurization and dispensing system of claim 1, wherein the pressurized gas composition cartridge comprises one or more of the following: a disposable pre-pressurized $N_2$ and $CO_2$ blend gas composition cartridge, a disposable pre-pressurized $N_2$ gas composition cartridge, a disposable pre-pressurized $CO_2$ gas composition cartridge, a disposable pre-pressurized argon gas composition cartridge.

21. The fluid pressurization and dispensing system of claim 1, wherein the pressurized gas composition cartridge comprises one or more of the following: a refillable pre-pressurized 70% $N_2$ and 30% $CO_2$ blend gas composition cartridge, a refillable pre-pressurized 75% $N_2$ and 25% $CO_2$ blend gas composition cartridge.

22. The fluid pressurization and dispensing system of claim 1, wherein the gas injection aperture is compatible with pre-pressurized gas compositions cartridges including one or more of the following: 6 grams, 8 grams, 12 grams, 16 grams, 25 grams, and 33 grams.

23. The fluid pressurization and dispensing system of claim 1, wherein the gas injection aperture includes an integrally machined threaded male opening adapted and operable for releasably attaching a threaded female opening of a pre-pressurized gas composition cartridge.

24. The fluid pressurization and dispensing system of claim 1, wherein the gas injection aperture includes an integrally machined threaded female opening adapted and operable for releasably attaching a threaded male opening of a pre-pressurized gas composition cartridge.

25. The fluid pressurization and dispensing system of claim 1, wherein the coupler includes two gas injection apertures integrally machined within the coupler for enabling releasably attaching simultaneously a first pre-pressurized gas composition cartridge having a female attachment means and releasably attaching a second pre-pressurized gas composition cartridge having a male attachment means adapted for enabling transmission of a blended flow of gas composition into the vessel.

26. The fluid pressurization and dispensing system of claim 1, wherein the faucet is a faucet selected from the group comprising of, a standard, a ventless with shaft, a ventless without shaft, a nitro-faucet, and a spring loaded cam-actuated, and a roto-faucet.

27. The fluid pressurization and dispensing system of claim 1, wherein the faucet includes a faucet adaptor adapted for releasably attaching a European beer faucet.

28. The fluid pressurization and dispensing system of claim 1, wherein the faucet includes a faucet adaptor adapted for releasably attaching a flow control faucet.

29. The fluid pressurization and dispensing system of claim 1, wherein the faucet is a stout faucet comprising a removable restrictor plate adapted and operable for regulating the flow of the fluid through the faucet.

30. The fluid pressurization and dispensing system of claim 1, wherein the fluid contained within the vessel comprises a fluid selected from the group comprising of: a pressurized liquid beverage, a carbonated liquid beverage, a non-carbonated liquid beverage, and a nitrogenated liquid beverage.

31. The fluid pressurization and dispensing system of claim 1, wherein the fluid contained within the vessel comprises a gas.

32. The fluid pressurization and dispensing system of claim 1, wherein the vessel comprises a 1 gallon vessel capable of being pre-pressurized.

33. The fluid pressurization and dispensing system of claim 1, wherein the vessel comprises a 2 gallon vessel capable of being pre-pressurized.

34. The fluid pressurization and dispensing system of claim 1, wherein the vessel is a beer vessel capable of being pre-pressurized.

35. The fluid pressurization and dispensing system of claim 1, wherein the vessel is a wine vessel capable of being pre-pressurized.

36. The fluid pressurization and dispensing system of claim 1, wherein the vessel is a soda vessel capable of being pre-pressurized.

37. The fluid pressurization and dispensing system of claim 1, wherein the vessel further includes a chime permanently mounted to the shoulder portion of the vessel, the chime including a bottom handle ring having a circumference $C^1$ and a top handle ring having a circumference $C^2$ which is greater than the circumference $C^1$ of the bottom handle ring, the bottom handle ring joined to the top handle ring via a plurality of rigid spokes outwardly extending from the bottom handle ring to the top handle ring, each rigid spoke having an equal height $h^3$ and equally spaced separate and apart from each other a base length $b_1$ measured along the bottom handle ring and a base length $b_2$ measured along the top handle ring such that a plurality of handle spaces are formed having generally a trapezoid shape adapted and operable for facilitating hand holds.

38. The fluid pressurization and dispensing system of claim 37, wherein the top handle ring further includes a at least one curve along an edge of the top handle ring for conforming in shape to a fluid receptacle to be supported in contacting relation therealong when the fluid is dispensed from the faucet into the fluid receptacle.

39. The fluid pressurization and dispensing system of claim 1, wherein the coupler is manufactured from a food-grade material comprising stainless steel.

40. The fluid pressurization and dispensing system of claim 1, wherein the vessel is manufactured from a food-grade material comprising stainless steel.

41. The fluid pressurization and dispensing system of claim 1, wherein the fluid delivery tube is manufactured from a food-grade tubing material selected from the group comprising of: a polyethylene tubing, a barrier tubing, a polymer tubing, and a stainless steel tubing.

42. The fluid pressurization and dispensing system of claim 1, wherein the gas pressure relief valve is a Belleville type spring including a Belleville spring washer held by an elastomeric hinge and operable to automatically open once a predetermined gas pressure is achieved.

43. The fluid pressurization and dispensing system of claim 1, wherein the gas pressure relief valve comprises an elastomeric duckbill valve.

44. The fluid pressurization and dispensing system of claim 1, wherein the gas pressure relief valve comprises an umbrella valve.

45. The fluid pressurization and dispensing system of claim 1, wherein the gas pressure relief valve comprises a duckbill/umbrella combination valve.

46. The fluid pressurization and dispensing system of claim 1, wherein the gas pressure relief valve is adapted to maintain an internal pressure within the vessel within a pre-determined range of about 7 psi-60 psi.

47. The fluid pressurization and dispensing system of claim 1, wherein the gas pressure relief valve is adapted to maintain an internal pressure within the vessel within a pre-determined range of about 16 psi-60 psi.

48. The fluid pressurization and dispensing system of claim 1, wherein the plug includes the plug finish having an integrally machined exterior threads mateable with an integrally machined interior threads of the neck finish of the neck adapted for releasably attaching the coupler to the vessel.

49. The fluid pressurization and dispensing system of claim 1, wherein the plug includes the plug finish having an integrally machined interior threads which are mateable with an integrally machined exterior threads of the neck finish of the neck for enabling releasably attaching the coupler to the vessel.

50. The fluid pressurization and dispensing system of claim 1, wherein the plug of the coupler includes a non-threaded plug finish mateable with a non-threaded neck finish of the neck of the vessel for enabling releasably attaching the coupler to the vessel.

51. The fluid pressurization and dispensing system of claim 1, wherein the coupler is portable and transferable for use with a plurality of conventional vessels for containing liquid beverages, wherein the coupler includes an attachment means for enabling releasably attaching to a plurality of conventional vessels.

52. The fluid pressurization and dispensing system of claim 1, wherein the gas pressure regulator is self-regulating.

53. The fluid pressurization and dispensing system of claim 1, wherein the gas pressure regulator is manually regulated by the user.

54. The fluid pressurization and dispensing system of claim 1, wherein the faucet includes indicia provided thereon for identifying the fluid contained within the vessel.

55. The fluid pressurization and dispensing system of claim 1, wherein the pressurized gas composition cartridge is color coded such that a designated color identifies a type of fluid contained within the vessel.

56. The fluid pressurization and dispensing system of claim 1, wherein the pressurized gas composition cartridge includes a flavor to be implemented into the fluid contained within the vessel.

57. The fluid pressurization and dispensing system of claim 1, wherein the pressurized gas composition cartridge provides a pre-pressurized gas composition to clean out the plurality of channels machined within the coupler and the interior of the vessel.

* * * * *